(12) United States Patent
Fukazawa et al.

(10) Patent No.: US 12,167,828 B2
(45) Date of Patent: Dec. 17, 2024

(54) IMAGE PROCESSING APPARATUS, IMAGE PROCESSING METHOD, AND IMAGE PROCESSING SYSTEM FOR IMPROVING VISIBILITY OF INDOCYANINE GREEN IMAGE

(71) Applicant: SONY CORPORATION, Tokyo (JP)

(72) Inventors: Kentaro Fukazawa, Tokyo (JP); Takanori Fukazawa, Kanagawa (JP); Daisuke Kikuchi, Kanagawa (JP); Minori Takahashi, Kanagawa (JP); Kazuki Ikeshita, Saitama (JP)

(73) Assignee: SONY CORPORATION, Tokyo (JP)

( * ) Notice: Subject to any disclaimer, the term of this patent is extended or adjusted under 35 U.S.C. 154(b) by 458 days.

(21) Appl. No.: 16/761,490

(22) PCT Filed: Aug. 27, 2018

(86) PCT No.: PCT/JP2018/031471
§ 371 (c)(1),
(2) Date: May 4, 2020

(87) PCT Pub. No.: WO2019/092950
PCT Pub. Date: May 16, 2019

(65) Prior Publication Data
US 2021/0169305 A1 Jun. 10, 2021

(30) Foreign Application Priority Data
Nov. 13, 2017 (JP) .................. 2017-218465

(51) Int. Cl.
*A61B 1/00* (2006.01)
*G06T 7/00* (2017.01)

(52) U.S. Cl.
CPC .. *A61B 1/000094* (2022.02); *A61B 1/000095* (2022.02); *G06T 7/0012* (2013.01);
(Continued)

(58) Field of Classification Search
CPC .......... A61B 1/00009; A61B 1/000094; A61B 1/000095; A61B 1/043;
(Continued)

(56) References Cited

U.S. PATENT DOCUMENTS 6,421,454 B1 * 7/2002 Burke .................. A61B 6/5247
382/131
6,483,538 B2 * 11/2002 Hu ........................... G06T 7/32
348/189
(Continued)

FOREIGN PATENT DOCUMENTS

CN 102247115 A 11/2011
CN 103501681 A 1/2014
(Continued)

OTHER PUBLICATIONS

International Search Report and Written Opinion of PCT Application No. PCT/JP2018/031471, issued on Nov. 13, 2018, 10 pages of ISRWO.
(Continued)

*Primary Examiner* — Gandhi Thirugnanam
(74) *Attorney, Agent, or Firm* — CHIP LAW GROUP

(57) ABSTRACT

Provided is an image processing apparatus that includes a feature detecting unit that detects a feature of first image data, where the first image data is obtained by capturing an image of a blood vessel by IndoCyanine Green (ICG) fluorescence imaging. The image processing apparatus further includes an enhancement processing unit that controls a degree of an enhancement process performed on the first image data, on the basis of the feature.

19 Claims, 19 Drawing Sheets

(52) U.S. Cl.
CPC ............... *G06T 2207/10064* (2013.01); *G06T 2207/10068* (2013.01); *G06T 2207/30101* (2013.01)

(58) Field of Classification Search
CPC . G06T 2207/10064; G06T 2207/10068; G06T 2207/10152; G06T 2207/30101; G06T 5/008; G06T 7/0012; G06T 5/50; G06T 2207/20224; G06T 2207/20221
See application file for complete search history.

(56) References Cited

U.S. PATENT DOCUMENTS

| | | | |
|---|---|---|---|
| 2002/0097342 A1* | 7/2002 | Hu | G06T 7/32 348/700 |
| 2009/0147096 A1* | 6/2009 | Yamaguchi | A61B 1/0623 348/222.1 |
| 2009/0247881 A1* | 10/2009 | Maeda | A61B 5/489 600/476 |
| 2010/0054576 A1* | 3/2010 | Tsujita | A61B 1/000094 382/134 |
| 2011/0245642 A1* | 10/2011 | Minetoma | A61B 1/0655 600/324 |
| 2012/0154566 A1* | 6/2012 | Kaku | A61B 1/005 348/E7.085 |
| 2013/0176411 A1* | 7/2013 | Igarashi | A61B 1/0638 348/65 |
| 2015/0042774 A1* | 2/2015 | Sugano | H04N 23/80 348/68 |
| 2015/0339814 A1* | 11/2015 | Oishi | G06T 11/00 382/131 |
| 2017/0258296 A1* | 9/2017 | Kaku | A61B 1/3137 |
| 2018/0084997 A1* | 3/2018 | Umezawa | A61B 5/14542 |
| 2018/0085005 A1* | 3/2018 | Umezawa | G06T 5/50 |
| 2019/0021579 A1* | 1/2019 | Kamon | A61B 5/14551 |
| 2019/0378285 A1* | 12/2019 | Niskanen | G06T 7/37 |
| 2021/0169305 A1* | 6/2021 | Fukazawa | A61B 1/000094 |

FOREIGN PATENT DOCUMENTS

| | | |
|---|---|---|
| EP | 2466874 A2 | 6/2012 |
| EP | 2687145 A1 | 1/2014 |
| EP | 3251582 A1 | 12/2017 |
| JP | 2010-051350 A | 3/2010 |
| JP | 2011-005002 A | 1/2011 |
| JP | 2011-087906 A | 5/2011 |
| JP | 2011-217798 A | 11/2011 |
| JP | 2012-125461 A | 7/2012 |
| JP | 2015-029841 A | 2/2015 |
| JP | 2015-066311 A | 4/2015 |
| JP | 2015-223210 A | 12/2015 |
| JP | 2016-144626 A | 8/2016 |
| JP | 2016-158838 A | 9/2016 |
| WO | 2013/042395 A1 | 3/2013 |

OTHER PUBLICATIONS

Frangi, et al., "Multiscale vessel enhancement filtering", Proceedings of MICCAI, 1998, pp. 130-137.

* cited by examiner

FIG.6

| ABSOLUTE VALUE OF CORRELATION VALUE | DEGREE OF SCATTERING (LARGER VALUE INDICATES LARGER SCATTERING) |
|---|---|
| 0~0.5 | 2 |
| 0.5~0.8 | 1 |
| 0.8~1.0 | 0 |

| ABSOLUTE VALUE OF DIFFERENCE VALUE | VASCULAR DIAMETER (LARGER VALUE INDICATES SMALLER VASCULAR DIAMETER) |
|---|---|
| 0.8~1.0 | 2 |
| 0.5~0.8 | 1 |
| 0~0.5 | 0 |

1125 f(x,y)

σ=0.5

σ=5

σ=10

σ=15

σ=20

| RATIO OF BLOOD VESSELS | MOST-FREQUENT VASCULAR DIAMETER | VASCULAR DENSITY (LARGER VALUE INDICATES HIGHER DENSITY) |
|---|---|---|
| 0.8~1.0 | 2(THIN) | 2 |
| | 1(MEDIUM) | 1 |
| | 0(THICK) | 0 |
| 0.2~0.8 | 2(THIN) | 1 |
| | 1(MEDIUM) | 0 |
| | 0(THICK) | 0 |
| 0.0~0.2 | 2(THIN) | 0 |
| | 1(MEDIUM) | 0 |
| | 0(THICK) | 0 |

1132

| BLOOD VESSEL INFORMATION | CORRELATION VALUE | VASCULAR DEPTH (LARGER VALUE INDICATES DEEPER DEPTH) |
|---|---|---|
| BLOOD VESSEL IS PRESENT | 0~0.5 | 2 |
| | 0.5~0.8 | 1 |
| | 0.8~1.0 | 0 |
| BLOOD VESSEL IS ABSENT | 0~0.5 | 4 |
| | 0.5~0.8 | 3 |
| | 0.8~1.0 | 0 |

1144

IMAGE PROCESSING APPARATUS, IMAGE PROCESSING METHOD, AND IMAGE PROCESSING SYSTEM FOR IMPROVING VISIBILITY OF INDOCYANINE GREEN IMAGE

CROSS REFERENCE TO RELATED APPLICATIONS

This application is a U.S. National Phase of International Patent Application No. PCT/JP2018/031471 filed on Aug. 27, 2018, which claims priority benefit of Japanese Patent Application No. JP 2017-218465 filed in the Japan Patent Office on Nov. 13, 2017. Each of the above-referenced applications is hereby incorporated herein by reference in its entirety.

FIELD

The present disclosure relates to an image processing apparatus, an image processing method, and an image processing system.

BACKGROUND

In recent years, an endoscope is sometimes used in medical practice. When an image is captured by the endoscope, normal observation to observe a normal image that is obtained by applying white light may be performed in some cases. Alternatively, in some other cases, fluorescence observation to obtain an image (fluorescence image) by fluorescence that is generated by applying excitation light may be performed. Further, a technique for displaying, on a monitor, a composite image in which the normal image and the fluorescence image are superimposed on each other has been disclosed (for example, see Patent Literature 1).

CITATION LIST

Patent Literature

Patent Literature 1: Japanese Laid-open Patent Publication No. 2011-5002

SUMMARY

Technical Problem

The fluorescence image obtained as described above is subjected to an enhancement process and thereafter displayed on a monitor. In this case, if a degree of the enhancement process on the fluorescence image input from a camera head is uniform, in some regions, the degree of the enhancement process may be too intense and visibility is not improved. As one example, it is acceptable to increase the degree of the enhancement process to be subjected to a region with large scattering and a thin blood vessel, but if the same degree of the enhancement process is performed on other regions, the degree of the enhancement process may be too intense.

Therefore, it is desired to provide a technology capable of improving visibility of a fluorescence image.

Solution to Problem

According to the present disclosure, an image processing apparatus is provided that includes: a feature detecting unit configured to detect a feature of first image data that is obtained by capturing an image of a blood vessel by ICG fluorescence imaging; and an enhancement processing unit configured to control a degree of an enhancement process performed on the first image data, on the basis of the feature.

According to the present disclosure, an image processing method is provided that includes: detecting a feature of first image data that is obtained by capturing an image of a blood vessel by ICG fluorescence imaging; and controlling, by a processor, a degree of an enhancement process performed on the first image data, on the basis of the feature.

According to the present disclosure, an image processing system is provided that includes: an imaging unit configured to capture an image of a blood vessel by ICG fluorescence imaging and obtain first image data; a feature detecting unit configured to detect a feature of the first image data; and an enhancement processing unit configured to control a degree of the enhancement process performed on the first image data on the basis of the feature.

Advantageous Effects of Invention

As described above, according to the present disclosure, a technology capable of improving visibility of a fluorescence image is provided. Meanwhile, the effects described above are not limitative, and, with or in the place of the above effects, any of the effects described in this specification or other effects that can be recognized from this specification may be achieved.

BRIEF DESCRIPTION OF DRAWINGS

FIG. 6 is a diagram illustrating an example of a correspondence relationship between a correlation value and a degree of scattering.

DESCRIPTION OF EMBODIMENTS

Preferred embodiments of the present disclosure will be described in detail below with reference to the accompanying drawings. In this specification and the drawings, structural elements that have substantially the same functions and configurations will be denoted by the same reference symbols, and repeated explanation of the structural elements will be omitted.

Further, in this specification and the drawings, a plurality of structural elements that have substantially the same or similar functions and configurations may be distinguished from one another by appending different numbers after the same reference symbols. However, if the structural elements that have substantially the same or similar functions and configurations need not be specifically distinguished from one another, the structural elements will be denoted by only the same reference symbols. Furthermore, similar structural elements in different embodiments may be distinguished from one another by appending different alphabets after the same reference symbols. However, if the similar structural elements need not be specifically distinguished from one another, the structural elements will be denoted by only the same reference symbols.

In addition, hereinafter, explanation will be given in the following order.
1. System configuration example
2. Overview
3. First Embodiment
4. Second Embodiment
5. Conclusion 1. System Configuration Example First, a configuration example as one example of a medical system (image processing system) according to an embodiment of the present disclosure will be described with reference to the drawings. Examples of the medical system according to the embodiment of the present disclosure include various systems. Here, as one example of the medical system according to the embodiment of the present disclosure, a configuration example of an endoscopic surgery system will be mainly described.

Figure 1:
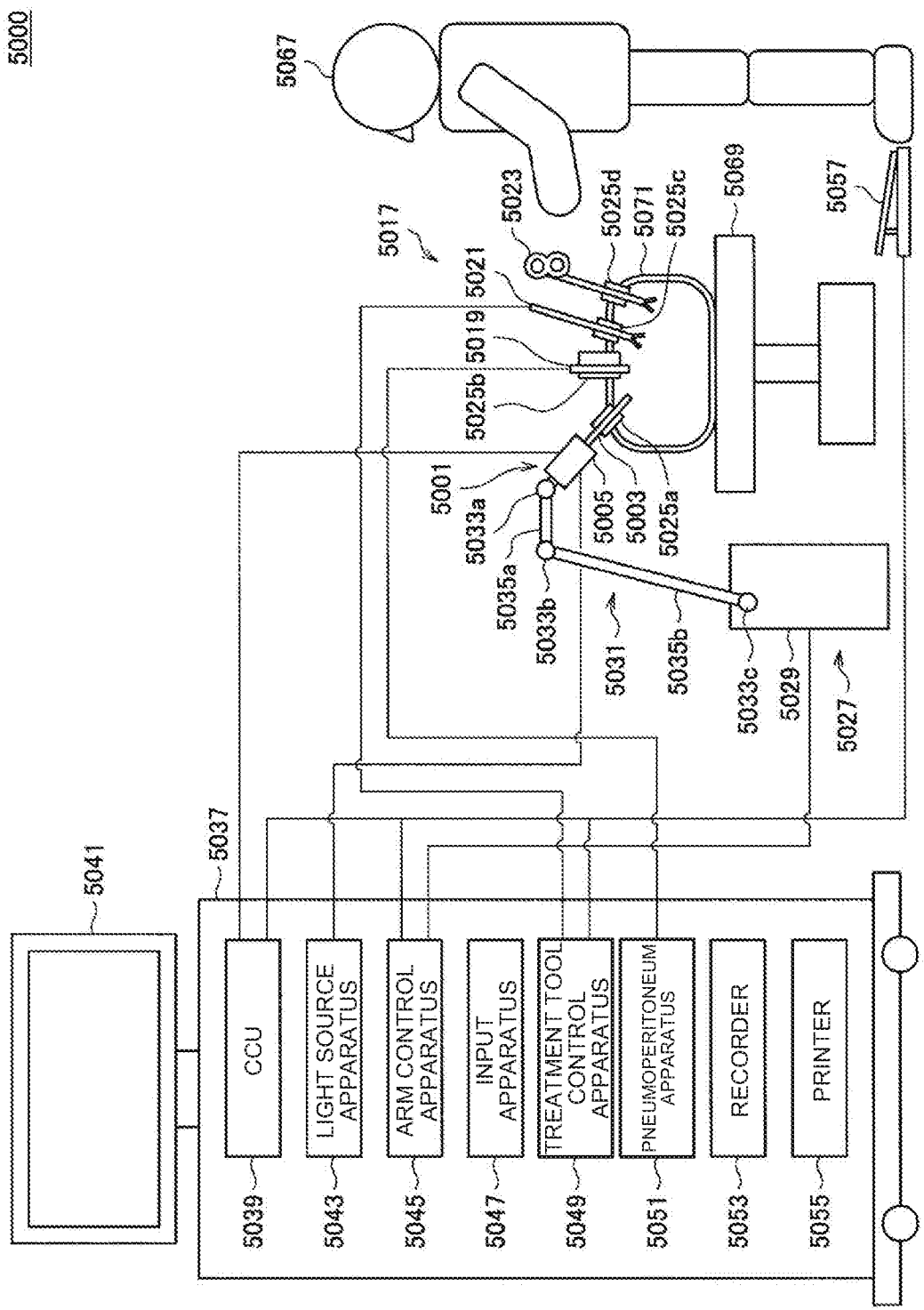
FIG. 1 is a diagram illustrating an example of a schematic configuration of an endoscopic surgery system.

FIG. 1 is a diagram illustrating an example of a schematic configuration of an endoscopic surgery system 5000 to which a technology according to the present disclosure is adopted. In FIG. 1, a state is illustrated in which a surgeon (doctor) 5067 performs surgery on a patient 5071 on a patient bed 5069 by using the endoscopic surgery system 5000. As illustrated in the figure, the endoscopic surgery system 5000 includes an endoscope 5001, other surgery tools 5017, a support arm apparatus 5027 that supports the endoscope 5001, and a cart 5037 on which various apparatuses for endoscopic surgery are mounted.

In the endoscopic surgery, cylindrical drilling tools called trocars 5025a to 5025d are introduced to make a plurality of punctures into an abdominal wall, instead of opening an abdominal cavity by cutting the abdominal wall. Then, a lens barrel 5003 of the endoscope 5001 and the other surgery tools 5017 are inserted into a body cavity of the patient 5071 through the trocars 5025a to 5025d. In the example illustrated in the figure, an insufflation tube 5019, an energy treatment tool 5021, and a forceps 5023 are inserted, as the other surgery tools 5017, into the body cavity of the patient 5071. Further, the energy treatment tool 5021 is a treatment tool for cutting and loosening tissue, sealing a blood vessel, and the like with high-frequency current or ultrasonic vibration. However, the surgery tools 5017 illustrated in the drawing are mere examples, and, as the surgery tools 5017, for example, various surgery tools, such as a tweezer and a retractor, which are generally used in the endoscopic surgery, may be used.

An image of a surgical site inside the body cavity of the patient 5071 captured by the endoscope 5001 is displayed on a display apparatus 5041. The surgeon 5067 views the image of the surgical site displayed on the display apparatus 5041 in real time and performs treatment, such as removal of an affected area, using the energy treatment tool 5021 or the forceps 5023. While not illustrated in the figure, the insufflation tube 5019, the energy treatment tool 5021, and the forceps 5023 are supported by the surgeon 5067, an assistant, or the like during the surgery.

(Support Arm Apparatus)

The support arm apparatus 5027 includes an arm section 5031 that extends from a base section 5029. In the example illustrated in the drawing, the arm section 5031 includes joint sections 5033a, 5033b, and 5033c, and links 5035a and 5035b, and is driven by being controlled by an arm control apparatus 5045. The arm section 5031 supports the endoscope 5001 and controls a position and posture of the endoscope 5001. With this configuration, it is possible to stably fix the position of the endoscope 5001.

(Endoscope)

The endoscope 5001 includes the lens barrel 5003, a certain region of which with a predetermined length from a distal end is to be inserted into the body cavity of the patient 5071, and a camera head 5005, which is connected to a proximal end of the lens barrel 5003. In the example illustrated in the drawing, the endoscope 5001 that is configured as what is called a rigid scope having the rigid lens barrel 5003 is illustrated; however, the endoscope 5001 may be configured as what is called a flexible scope having the flexible lens barrel 5003.

An opening in which an objective lens is fitted is arranged on the distal end of the lens barrel 5003. A light source apparatus 5043 is connected to the endoscope 5001, and light generated by the light source apparatus 5043 is guided to the distal end of the lens barrel by a light guide that is extended inside the lens barrel 5003, and applied to an observation target inside the body cavity of the patient 5071 via the objective lens. The endoscope 5001 may be a forward-viewing endoscope, a forward-oblique viewing endoscope, or a side-viewing endoscope.

An optical system and an imaging element are arranged inside the camera head 5005, and the optical system condenses reflected light (observation light) from the observation target toward the imaging element. The imaging element performs photoelectric conversion on the observation light, and an electrical signal corresponding to the observation light, that is, an image signal corresponding to an observation image, is generated. The image signal is transmitted, as RAW data, to a camera control unit (CCU) 5039. The camera head 5005 has a function to adjust a magnification and a focal length by appropriately driving the optical system.

To cope with a stereoscopic view (3D-display) or the like for example, it may be possible to arrange a plurality of imaging elements on the camera head 5005. In this case, a plurality of relay optical systems are arranged inside the lens barrel 5003 in order to guide the observation light to the respective imaging elements.

(Various Apparatuses Mounted on Cart)

The CCU 5039 is constructed by a central processing unit (CPU), a graphics processing unit (GPU), or the like, and integrally controls operation of the endoscope 5001 and the display apparatus 5041. Specifically, the CCU 5039 performs various kinds of image processing, such as a developing process (demosaicing process), on the image signal received from the camera head 5005, in order to display an image based on the image signal. The CCU 5039 provides the image signal subjected to the image processing to the display apparatus 5041. Further, the CCU 5039 transmits a control signal to the camera head 5005 and controls drive of the camera head 5005. The control signal may include information on imaging conditions, such as the magnification and the focal length.

The display apparatus 5041 displays the image based on the image signal subjected to the image processing by the CCU 5039, under the control of the CCU 5039. If the endoscope 5001 is compatible with high-resolution imaging, such as 4K (3840 horizontal pixels×2160 vertical pixels) or 8K (7680 horizontal pixels×4320 vertical pixels), and/or if the endoscope 5001 is compatible with 3D-display, an apparatus that can perform high-resolution display and/or 3D-display is used as the display apparatus 5041 in accordance with the respective compatibilities. If the apparatus is compatible with high-resolution imaging, such as 4K or 8K, it is possible to achieve increased immersion by adopting an apparatus with a size of 55 inch or larger as the display apparatus 5041. Further, it may be possible to arrange the plurality of display apparatuses 5041 with different resolution and sizes for different uses.

The light source apparatus 5043 is constructed by a light source, such as a light emitting diode (LED), and supplies illumination light for capturing an image of a surgical site to the endoscope 5001.

The arm control apparatus 5045 is constructed by a processor, such as a CPU, operates in accordance with a predetermined program, and controls drive of the arm section 5031 of the support arm apparatus 5027 in accordance with a predetermined control method.

An input apparatus 5047 is an input interface for the endoscopic surgery system 5000. A user is able to input various kinds of information and instructions to the endoscopic surgery system 5000 via the input apparatus 5047. For example, the user inputs, via the input apparatus 5047, various kinds of information on surgery, such as body information on a patient or information on procedures of the surgery. Further, for example, the user inputs, via the input apparatus 5047, an instruction to drive the arm section 5031, an instruction to change imaging conditions (a type of illumination light, the magnification, the focal length, and the like) of the endoscope 5001, an instruction to drive the energy treatment tool 5021, and the like.

Types of the input apparatus 5047 are not specifically limited, and various known input apparatuses may be adopted as the input apparatus 5047. As the input apparatus 5047, for example, a mouse, a keyboard, a touch panel, a switch, a foot switch 5057, and/or a lever may be adopted. If the touch panel is used as the input apparatus 5047, the touch panel may be arranged on a display surface of the display apparatus 5041.

Alternatively, the input apparatus 5047 may be, for example, a device that can be worn by the user, such as a glasses wearable device or a head mounted display (HMD), and various kinds of input are performed in accordance with gestures and lines of sight of the user detected by the device. Further, the input apparatus 5047 includes a camera that can detect motions of the user, and performs various kinds of input in accordance with gestures and lines of sight of the user detected from videos captured by the camera. Furthermore, the input apparatus 5047 includes a microphone that can collect voice of the user, and performs various kinds of input based on voice via the microphone. In this manner, the input apparatus 5047 is configured to be able to input various kinds of information in a non-contact manner, so that it is possible to allow, in particular, a user (for example, the surgeon 5067) who is in a clean zone to operate apparatuses located in a dirty zone in a non-contact manner. Moreover, the user is able to operate devices without releasing his/her hand from a carrying surgery tool, so that it is possible to improve the convenience of the user.

A treatment tool control apparatus 5049 controls drive of the energy treatment tool 5021 for tissue ablation, incision, sealing of a blood vessel, or the like. A pneumoperitoneum apparatus 5051 feeds gas into the body cavity via the insufflation tube 5019 to inflate the body cavity of the patient 5071, to thereby ensure a visual field of the endoscope 5001 and ensure an operating space for the surgeon. A recorder 5053 is an apparatus that can record various kinds of information on surgery. A printer 5055 is an apparatus that can print various kinds of information on surgery in various formats, such as a text, an image, or a graph.

A particularly characteristic configuration of the endoscopic surgery system 5000 will be described in detail below.

(Support Arm Apparatus)

The support arm apparatus 5027 includes the base section 5029 as a base board, and the arm section 5031 extending from the base section 5029. In the example illustrated in the drawing, the arm section 5031 includes the plurality of joint sections 5033a, 5033b, and 5033c and the plurality of links 5035a and 5035b that are connected by the joint section 5033b; however, in FIG. 1, the configuration of the arm section 5031 is simplified for the sake of simplicity. In reality, shapes, numbers, and arrangement of the joint sections 5033a to 5033c, directions of rotation axes of the links 5035a and 5035b and the like may be appropriately set to achieve desired flexibility of the arm section 5031. For example, the arm section 5031 may be preferably configured to have flexibility of 6 levels or higher. With this configuration, it becomes possible to freely move the endoscope 5001 in a movable range of the arm section 5031, so that it is possible to insert the lens barrel 5003 of the endoscope 5001 from a desired direction into the body cavity of the patient 5071.

Actuators are arranged in the joint sections 5033a to 5033c, and the joint sections 5033a to 5033c are configured to be able to rotate around predetermined rotation axes in accordance with the drive of the actuators. The drive of the actuators is controlled by the arm control apparatus 5045, so that a rotation angle of each of the joint sections 5033a to 5033c is controlled and the drive of the arm section 5031 is controlled. Accordingly, it becomes possible to control the position and the posture of the endoscope 5001. In this case, the arm control apparatus 5045 is able to control the drive of the arm section 5031 using various well-known control method, such as force control or position control.

For example, when the surgeon 5067 appropriately inputs operation via the input apparatus 5047 (including the foot switch 5057), the arm control apparatus 5045 may appropriately control the drive of the arm section 5031 in accordance with the input operation, and the position and the posture of the endoscope 5001 may be controlled. With this control, it is possible to first move the endoscope 5001 arranged on a distal end of the arm section 5031 from an arbitrary position to another arbitrary position, and thereafter fixedly support the endoscope 5001 at the moved position. The arm section 5031 may be operated by what is called a master-slave system. In this case, the arm section 5031 may be remotely operated by the user via the input apparatus 5047 that is installed at a place away from the surgery room.

Further, if the force control is adopted, the arm control apparatus 5045 may perform what is called power assist control to receive an external force from the user and drive the actuator of each of the joint sections 5033a to 5033c such that the arm section 5031 smoothly moves in accordance with the external force. With this configuration, when the user moves the arm section 5031 while directly touching the arm section 5031, it is possible to move the arm section 5031 with a relatively small force. Therefore, it becomes possible to more intuitively move the endoscope 5001 with easier operation, so that it is possible to improve the convenience of the user.

Here, in general, in endoscopic surgery, the endoscope 5001 is supported by a doctor called a scopist. In contrast, with use of the support arm apparatus 5027, it becomes possible to more reliably fix the position of the endoscope 5001 without manual intervention, so that it becomes possible to stably obtain an image of a surgical site and perform surgery smoothly.

Meanwhile, the arm control apparatus 5045 need not always be mounted on the cart 5037. Further, the arm control apparatus 5045 need not always be a single apparatus. For example, the arm control apparatus 5045 may be mounted on each of the joint sections 5033a to 5033c of the arm section 5031 of the support arm apparatus 5027, and the plurality of arm control apparatuses 5045 may operate in cooperation with one another and control drive of the arm section 5031.

(Light Source Apparatus)

The light source apparatus 5043 supplies illumination light to the endoscope 5001 when an image of a surgical site is to be captured. The light source apparatus 5043 includes, for example, an LED, a laser light source, or a white light source that is constructed by a combination of an LED and a laser light source. In this case, if the white light source is constructed by a combination of RGB laser light sources, it is possible to control output intensity and an output timing of each of colors (each of wavelengths) with high accuracy, and therefore, in the light source apparatus 5043, it is possible to adjust a white balance of a captured image. Further, in this case, by illuminating an observation target with laser light from each of the RGB laser light sources in a time-sharing manner and controlling the drive of the imaging element of the camera head 5005 in synchronization with illumination timings, it is possible to capture respective images corresponding to RGB in a time-sharing manner. With this method, it is possible to obtain a color image without arranging a color filter on the imaging element.

Furthermore, it may be possible to control the drive of the light source apparatus 5043 such that the intensity of output light is changed at predetermined time intervals. By controlling the drive of the imaging element of the camera head 5005 in synchronization with a timing to change the intensity of light, obtaining images in a time-sharing manner, and combining the obtained images, it is possible to generate a high dynamic range image in which what is called blocked up shadows and blown out highlights do not occur.

Moreover, the light source apparatus 5043 may be configured to be able to supply light in a predetermined wavelength band corresponding to special light observation. In the special light observation, for example, what is called narrow band imaging is performed, in which light in a narrower band than that of illumination light (in other words, white light) used in normal observation is applied by using wavelength dependency of light absorption in body tissues and an image of a predetermined tissue, such as a blood vessel in a superficial portion of a mucous membrane, is captured with high contrast. Alternatively, in the special light observation, it may be possible to perform fluorescence observation to obtain an image by fluorescence that is generated by applying excitation light. In the fluorescence observation, it may be possible to perform observation (autofluorescence observation) in which a body tissue is illuminated with excitation light and fluorescence received from the body tissue is observed, or it may be possible to perform imaging by locally injecting reagent, such as indocyanine green (ICG), into a body tissue, illuminating the body tissue with excitation light corresponding to a fluorescence wavelength of the reagent, and acquiring a fluorescent image, for example. The light source apparatus 5043 may be configured to be able to supply the narrow band light and/or the excitation light corresponding to the special light observation as described above.

(Camera Head and CCU)

Figure 2:
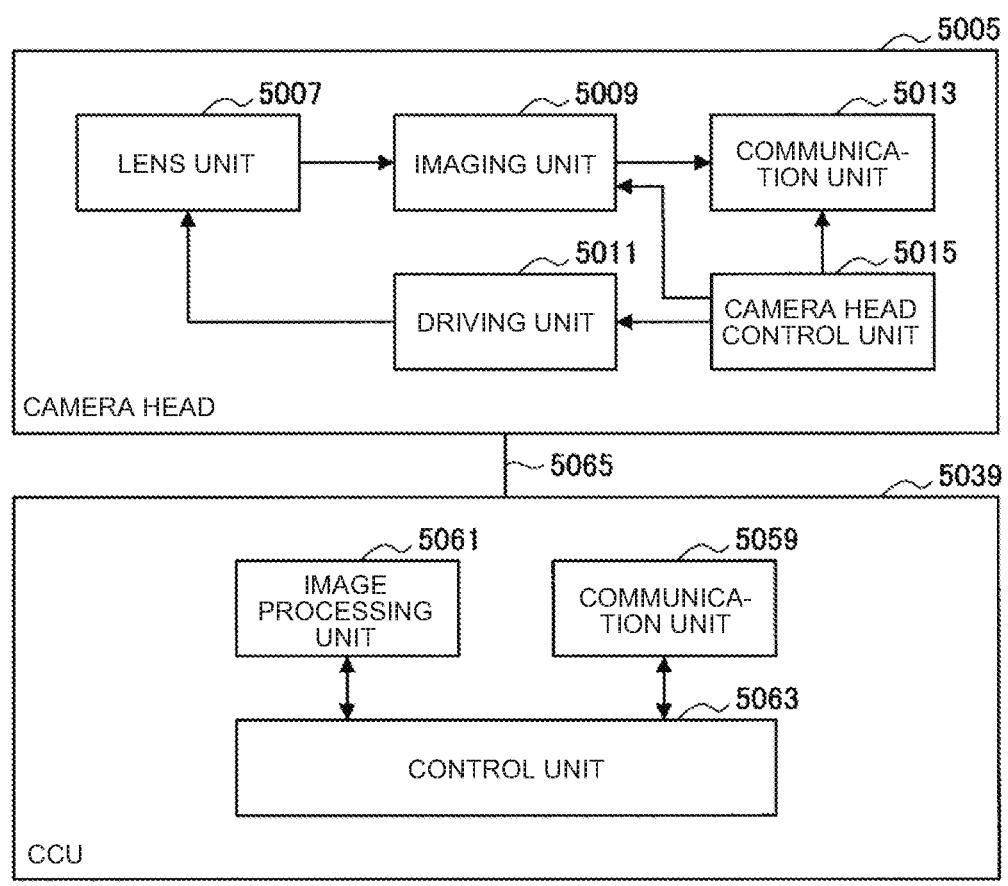
FIG. 2 is a block diagram illustrating an example of a functional configuration of a camera head and a CCU illustrated in FIG. 1.

Functions of the camera head 5005 and the CCU 5039 of the endoscope 5001 will be described in detail below with reference to FIG. 2. FIG. 2 is a block diagram illustrating an example of functional configurations of the camera head 5005 and the CCU 5039 illustrated in FIG. 1.

With reference to FIG. 2, the camera head 5005 includes, as the functions thereof, a lens unit 5007, an imaging unit 5009, a driving unit 5011, a communication unit 5013, and a camera head control unit 5015. Further, the CCU 5039 includes, as the functions thereof, a communication unit 5059, an image processing unit 5061, and a control unit 5063. The camera head 5005 and the CCU 5039 are connected to each other such that they can bi-directionally communicate with each other via a transmission cable 5065.

First, the functional configuration of the camera head 5005 will be described. The lens unit 5007 is an optical system arranged in a connection part connected to the lens barrel 5003. Observation light that has entered from the distal end of the lens barrel 5003 is guided to the camera head 5005 and enters the lens unit 5007. The lens unit 5007 is constructed by a combination of a plurality of lenses including a zoom lens and a focus lens. Optical characteristics of the lens unit 5007 are adjusted such that observation light is condensed on a light-receiving surface of an imaging element of the imaging unit 5009. Further, the zoom lens and the focus lens are configured such that positions thereof on an optical axis can be moved to adjust a magnification and a focal point of a captured image.

The imaging unit 5009 is constructed by the imaging element and is arranged on a subsequent stage of the lens unit 5007. The observation light that has passed through the lens unit 5007 is condensed on the light-receiving surface of the imaging element, and an image signal corresponding to an observation image is generated through photoelectric conversion. The image signal generated by the imaging unit 5009 is provided to the communication unit 5013.

As the imaging element included in the imaging unit 5009, for example, a complementary metal oxide semiconductor (CMOS) type image sensor that has Bayer arrangement and that can capture color images may be used. Meanwhile, as the imaging element, for example, a device that is compatible with capturing of an image with high resolution of 4K or higher may be used. By obtaining an image of a surgical site at high resolution, the surgeon 5067 is able to more precisely recognize a condition of the surgical site, so that it is possible to perform the surgery more smoothly.

Further, the imaging element included in the imaging unit 5009 is configured to include a pair of imaging elements to obtain image signals for right and left eyes to cope with 3D-display. By performing 3D-display, the surgeon 5067 is able to accurately recognize a depth of a body tissue in the surgical site. If the imaging unit 5009 is configured as a multi-sensor system, the plurality of lens units 5007 are arranged in accordance with the respective imaging elements.

Furthermore, the imaging unit 5009 need not always be mounted on the camera head 5005. For example, the imaging unit 5009 may be arranged immediately after the objective lens inside the lens barrel 5003.

The driving unit 5011 is constructed by an actuator, and moves the zoom lens and the focus lens of the lens unit 5007 by a predetermined distance along the optical axis under the control of the camera head control unit 5015. Accordingly, it is possible to appropriately adjust a magnification and a focal point of a captured image captured by the imaging unit 5009.

The communication unit 5013 is constructed by a communication apparatus for transmitting and receiving various kinds of information to and from the CCU 5039. The communication unit 5013 transmits the image signal obtained from the imaging unit 5009 as RAW data to the CCU 5039 via the transmission cable 5065. In this case, to display the captured image of the surgical site with low latency, it is preferable to transmit the image signal through optical communication. The reason for this is as follows: when surgery is performed, the surgeon 5067 performs the surgery while observing a condition of an affected area using the captured image, and therefore, it is demanded to display a video of a surgical site in real time as best as possible to perform the surgery more safely and more reliably. When the optical communication is performed, a photoelectric conversion module that converts an electrical signal to an optical signal is arranged in the communication unit 5013. The image signal is converted to an optical signal by the photoelectric conversion module, and thereafter transmitted to the CCU 5039 via the transmission cable 5065.

Further, the communication unit 5013 receives, from the CCU 5039, a control signal for controlling drive of the camera head 5005. The control signal includes information on an imaging condition, such as information for designating a frame rate of a captured image, information for designating an exposure value at the time of imaging, and/or information for designating the magnification and the focal point of the captured image. The communication unit 5013 provides the received control signal to the camera head control unit 5015. Meanwhile, the control signal from the CCU 5039 may be transmitted through optical communication. In this case, a photoelectric conversion module that converts an optical signal to an electrical signal is arranged in the communication unit 5013, and the control signal is converted to an electrical signal by the photoelectric conversion module and thereafter provided to the camera head control unit 5015.

The imaging conditions as described above, such as the frame rate, the exposure value, the magnification, and the focal point, are automatically set by the control unit 5063 of the CCU 5039 on the basis of the acquired image signal. In other words, the endoscope 5001 is equipped with what is called an automatic exposure (AE) function, an automatic focus (AF) function, and an automatic white balance (AWB) function.

The camera head control unit 5015 controls the drive of the camera head 5005 on the basis of the control signal that is received from the CCU 5039 via the communication unit 5013. For example, the camera head control unit 5015 controls the drive of the imaging element of the imaging unit 5009 on the basis of the information for designating the frame rate of the captured image and/or the information for designating exposure at the time of imaging. Further, for example, the camera head control unit 5015 appropriately moves the zoom lens and the focus lens of the lens unit 5007 via the driving unit 5011 on the basis of the information for designating the magnification and the focal point of the captured image. The camera head control unit 5015 may further include a function to store information for identifying the lens barrel 5003 and the camera head 5005.

By arranging the components, such as the lens unit 5007 and the imaging unit 5009, inside a sealed structure with high air tightness and high waterproof property, it is possible to ensure resistance of the camera head 5005 to an autoclave sterilization process.

The functional configuration of the CCU 5039 will be described below. The communication unit 5059 is constructed by a communication apparatus for transmitting and receiving various kinds of information to and from the camera head 5005. The communication unit 5059 receives an image signal that is transmitted from the camera head 5005 via the transmission cable 5065. In this case, as described above, the image signal may be preferably transmitted through optical communication. In this case, to cope with the optical communication, a photoelectric conversion module that converts an optical signal to an electrical signal is arranged in the communication unit 5059. The communication unit 5059 provides the image signal converted to the electrical signal to the image processing unit 5061.

Further, the communication unit 5059 transmits a control signal for controlling the drive of the camera head 5005 to the camera head 5005. The control signal may be transmitted through optical communication.

The image processing unit 5061 performs various kinds of image processing on the image signal that is RAW data transmitted from the camera head 5005. Examples of the image processing include various kinds of well-known signal processing, such as a developing process, a high-quality image processing (band enhancement processing, super-resolution processing, noise reduction (NR) processing and/or shake correction processing), and/or enlargement processing (electronic zoom processing). Further, the image processing unit 5061 performs wave detection processing on the image signal to implement AE, AF, and AWB.

The image processing unit 5061 is constructed by a processor, such as a CPU or a GPU, and the processor operates in accordance with a predetermined program, so that the image processing and the wave detection processing as described above can be performed. If the image processing unit 5061 is constructed by a plurality of GPUs, the image processing unit 5061 appropriately divides information on the image signal, and performs image processing in parallel using the plurality of GPUs.

The control unit 5063 performs various kinds of control related to capturing of an image of a surgical site by the endoscope 5001 and display of the captured image. For example, the control unit 5063 generates a control signal for controlling the drive of the camera head 5005. In this case, if the user has input an imaging condition, the control unit 5063 generates the control signal based on the input performed by the user. Alternatively, if the endoscope 5001 has the AE function, the AF function, and the AWB function, the control unit 5063 appropriately calculates an optimal exposure value, an optimal focal length, and an optimal white balance in accordance with a result of the wave detection processing performed by the image processing unit 5061, and generates a control signal.

Further, the control unit 5063 causes the display apparatus 5041 to display an image of the surgical site on the basis of the image signal subjected to the image processing by the image processing unit 5061. In this case, the control unit 5063 recognizes various objects in the image of the surgical site by using various image recognition techniques. For example, by detecting a shape, a color, or the like of an edge of an object included in the image of the surgical site, the control unit 5063 is able to recognize a surgery tool, such as a forceps, a specific site of a living body, bleeding, mist in the case of use of the energy treatment tool 5021, and the like. The control unit 5063, when causing the display apparatus 5041 to display the image of the surgical site, displays various kinds of surgery support information in a superimposed manner on the image of the surgical site by using a recognition result. By displaying and providing the surgery support information in a superimposed manner for the surgeon 5067, it is possible to perform the surgery more safely and more reliably.

The transmission cable 5065 that connects the camera head 5005 and the CCU 5039 is an electrical signal cable corresponding to electrical signal communication, an optical fiber corresponding to optical communication, or a composite cable of the above-described cables.

In the example illustrated in the figure, communication is performed in a wired manner using the transmission cable 5065, but communication between the camera head 5005 and the CCU 5039 may be performed in a wireless manner. If the communication between the camera head 5005 and the CCU 5039 is performed in a wireless manner, it is not necessary to arrange the transmission cable 5065 in the surgery room, so that it is possible to resolve a situation in which movement of a medical staff in the surgery room is disturbed by the transmission cable 5065.

One example of the endoscopic surgery system 5000 to which the technology according to the present disclosure is applicable has been described above. In the description above, the endoscopic surgery system 5000 has been described as one example, but a system to which the technology according to the present disclosure can be adopted is not limited to this example. For example, the technology according to the present disclosure may be adopted to an examination flexible endoscope system or a microscopic surgery system.

Thus, the configuration example of the endoscopic surgery system 5000 to which the technology according to the present disclosure has been described above.

2. Overview

An overview of the technology according to the present disclosure will be described below. In medical practice, an endoscope is sometimes used. When an image is captured by the endoscope, normal observation to observe a normal image that is obtained by applying white light may be performed in some cases. Alternatively, in some other cases, fluorescence observation to obtain an image (fluorescence image) by fluorescence that is generated by applying excitation light may be performed. Further, a technique for displaying, on a monitor, a composite image in which the normal image and the fluorescence image are superimposed on each other has been disclosed.

The fluorescence image obtained as described above is displayed in some cases. In this case, if a degree of an enhancement process on the fluorescence image input from the camera head is uniform, in some regions, the degree of the enhancement process may be too intense and visibility is not improved. As one example, it is acceptable to increase the degree of the enhancement process to be subjected to a region with large scattering and a thin blood vessel, but if the same degree of the enhancement process is performed on other regions, the degree of the enhancement process may be too intense.

Therefore, in the embodiment of the present disclosure, a technology capable of improving visibility of a fluorescence image is proposed. Further, it is expected that improvement of the visibility of the fluorescence image leads to assistance for diagnosis of an observation target.

Thus, the overview of the technology according to the present disclosure has been described above.

3. First Embodiment

A first embodiment of the present disclosure will be described below.
(Functional Configuration Example of CCU)

Figure 3:
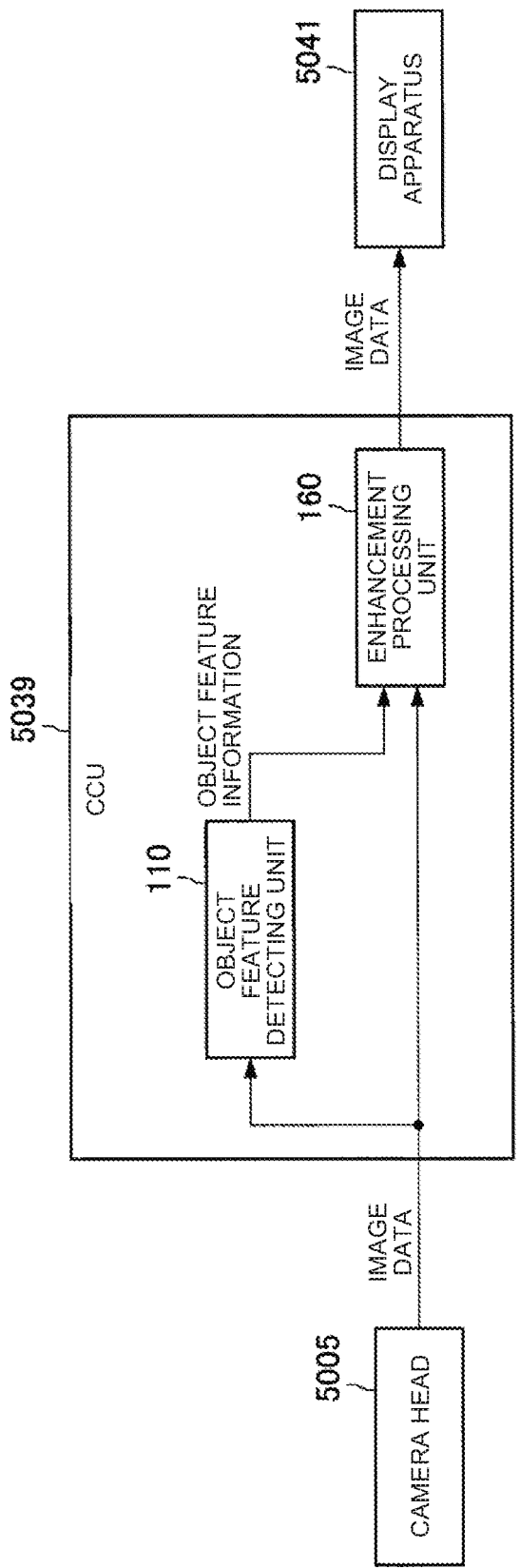
FIG. 3 is a block diagram illustrating a functional configuration example of the CCU according to a first embodiment of the present disclosure.

First, a functional configuration example of a CCU according to the first embodiment of the present disclosure will be described. FIG. 3 is a block diagram illustrating the functional configuration example of the CCU according to the first embodiment of the present disclosure. As illustrated in FIG. 3, the CCU 5039 according to the first embodiment of the present disclosure includes an object feature detecting unit 110 and an enhancement processing unit 160. The object feature detecting unit 110 and the enhancement processing unit 160 may be included in the image processing unit 5061 described above.

As described above, in the special light observation, fluorescence observation to obtain an image (fluorescence image) by fluorescence that is generated by applying excitation light may be performed. In the fluorescence observation, imaging (what is called ICG fluorescence imaging) may be performed to obtain a fluorescent image by locally injecting reagent, such as indocyanine green (ICG), into a body tissue, and illuminating the body tissue with excitation light corresponding to a fluorescence wavelength of the reagent. In the following, as one example of the fluorescence image, it is mainly assumed that first image data (hereinafter, also referred to as an "ICG image") that is obtained by capturing an image of a blood vessel by the ICG fluorescence imaging is input from the camera head 5005 to the CCU 5039.

Furthermore, as described above, in the normal observation, a normal image that is obtained by applying white light is observed. In the following, as one example of the normal image, it is mainly assumed that second image data (hereinafter, also referred to as a "while light image (WLI) image") that is obtained by capturing an image of a blood vessel by applying while light is input from the camera head 5005 to the CCU 5039.

When both of the ICG image and the WLI image are input from the camera head 5005 to the CCU 5039, an image sensor that captures the ICG image and an image sensor that captures the WLI image may be separated from each other. Alternatively, it may be possible to capture both of the ICG image and the WLI image by a common image sensor by switching between a timing to apply white light and a timing to apply excitation light by switching between types of light sources. Meanwhile, it is sufficient to input the ICG image to the CCU 5039, and it is sufficient to input the WLI image to the CCU 5039 as needed basis.

As illustrated in FIG. 3, the object feature detecting unit 110 (feature detecting unit) detects a feature (hereinafter, also referred to as "object feature information") of the ICG image. Then, the enhancement processing unit 160 controls a degree of an enhancement process to be performed on the ICG image, on the basis of the feature (object feature information) of the ICG image detected by the object feature detecting unit 110. With this configuration, it is possible to improve visibility of the ICG image that is one example of the fluorescence image.

The ICG image that is subjected to the enhancement process by the enhancement processing unit 160 is output to the display apparatus 5041 (display unit) via the control unit 5063. In this case, the control unit 5063 controls the display apparatus 5041 such that the ICG image subjected to the enhancement process is displayed on the display apparatus 5041. With this configuration, the user is able to view the ICG image subjected to the enhancement process.

It may be possible to display the ICG image before being subjected to the enhancement process by the enhancement processing unit 160 on the display apparatus 5041 via the control unit 5063, together with the ICG image after being subjected to the enhancement process by the enhancement processing unit 160. In this case, the control unit 5063 may control the display apparatus 5041 such that both of the ICG images before and after being subjected to the enhancement process are displayed on the display apparatus 5041. With this configuration, the user is able to visually compare the ICG images before and after being subjected to the enhancement process.

The degree of the enhancement process to be performed by the enhancement processing unit 160 may be changeable in accordance with operation performed by the user. In other words, the enhancement processing unit 160 may control the degree of the enhancement process on the basis of operation information input by the user. With this configuration, it is possible to adjust the degree of the enhancement process to be performed on the ICG image to a certain degree that is desired by the user. Meanwhile, the user may be able to input the operation information via the input apparatus 5047.

It may be possible to display the WLI image on the display apparatus 5041 via the control unit 5063, together with the ICG image subjected to the enhancement process by the enhancement processing unit 160. In this case, the control unit 5063 may control the display apparatus 5041 such that both of the ICG image subjected to the enhancement process and the WLI image are displayed on the display apparatus 5041. In this case, the ICG image subjected to the enhancement process and the WLI image may be displayed at separated positions, or the ICG image subjected to the enhancement process may be displayed in a superimposed manner on the WLI image.

Functions of the object feature detecting unit 110 and the enhancement processing unit 160 will be described in detail below.

(Object Feature Detecting Unit 110)

Figure 4:
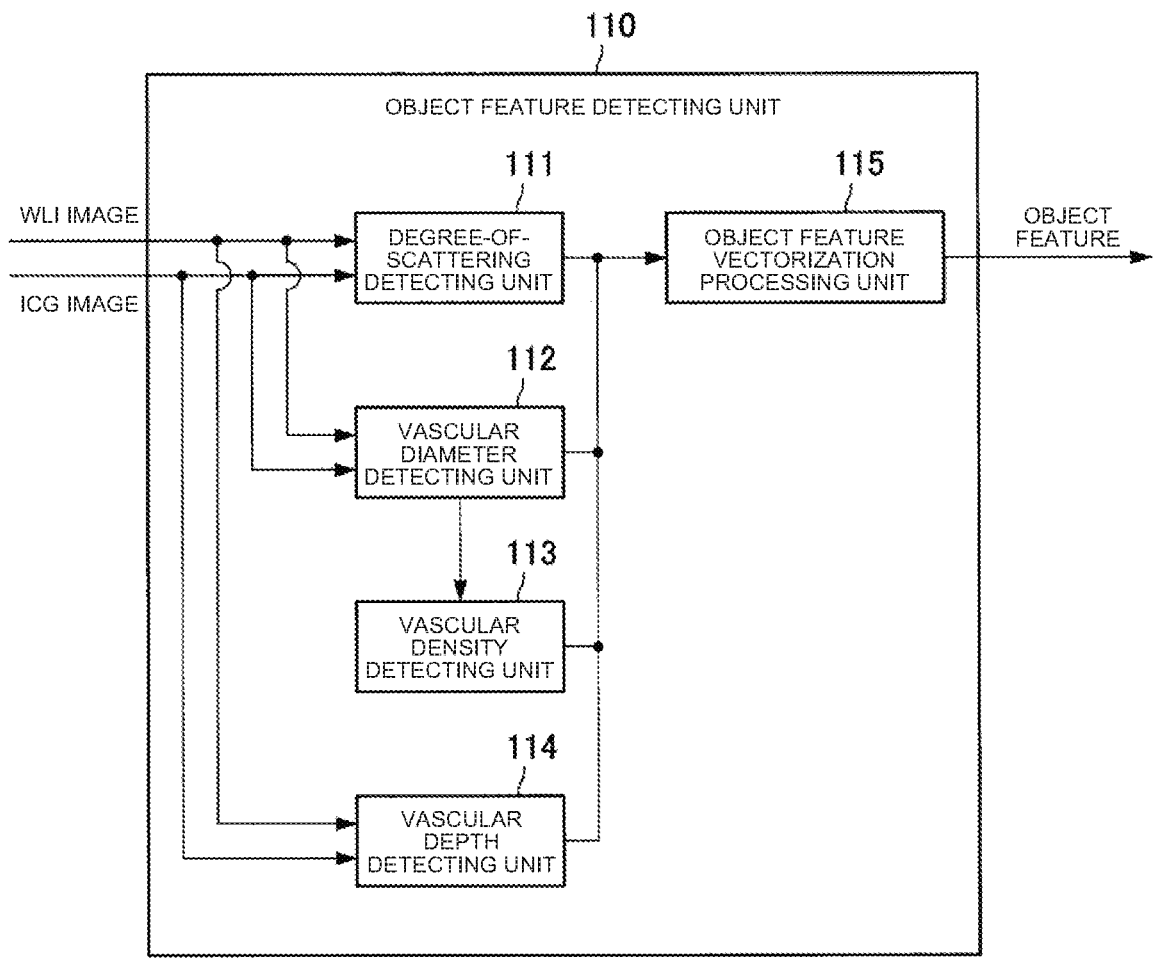
FIG. 4 is a diagram illustrating a detailed configuration example of an object feature detecting unit.

First, the functions of the object feature detecting unit 110 will be described in detail below. FIG. 4 is a diagram illustrating a detailed configuration example of the object feature detecting unit 110. As illustrated in FIG. 4, the object feature detecting unit 110 includes a degree-of-scattering detecting unit 111, a vascular diameter detecting unit 112, a vascular density detecting unit 113, a vascular depth detecting unit 114, and an object feature vectorization processing unit 115.

As will be described in detail later, the degree-of-scattering detecting unit 111 detects a degree of light scattering, the vascular diameter detecting unit 112 detects a vascular diameter, the vascular density detecting unit 113 detects a vascular density, and the vascular depth detecting unit 114 detects a vascular depth.

In the first embodiment of the present disclosure, it is mainly assumed that the object feature detecting unit 110 includes all of the degree-of-scattering detecting unit 111, the vascular diameter detecting unit 112, the vascular density detecting unit 113, and the vascular depth detecting unit 114. In this case, it is sufficient that the object feature vectorization processing unit 115 vectorizes the degree of scattering, the vascular diameter, the vascular density, and the vascular depth as an object feature. In other words, the object feature may include the degree of scattering, the vascular diameter, the vascular density, and the vascular depth.

However, the object feature detecting unit 110 may include only a part of the degree-of-scattering detecting unit 111, the vascular diameter detecting unit 112, the vascular density detecting unit 113, and the vascular depth detecting unit 114. In this case, it is sufficient to vectorize the part as the object feature. In other words, the object feature may include a part of the degree of scattering, the vascular diameter, the vascular density, and the vascular depth.

Meanwhile, if the object feature detecting unit 110 includes only one of the degree-of-scattering detecting unit 111, the vascular diameter detecting unit 112, the vascular density detecting unit 113, and the vascular depth detecting unit 114, the object feature vectorization processing unit 115 need not perform vectorization. In other words, the object feature may include one of the degree of scattering, the vascular diameter, the vascular density, and the vascular depth.

(Degree-of-Scattering Detecting Unit 111)

Figure 5:
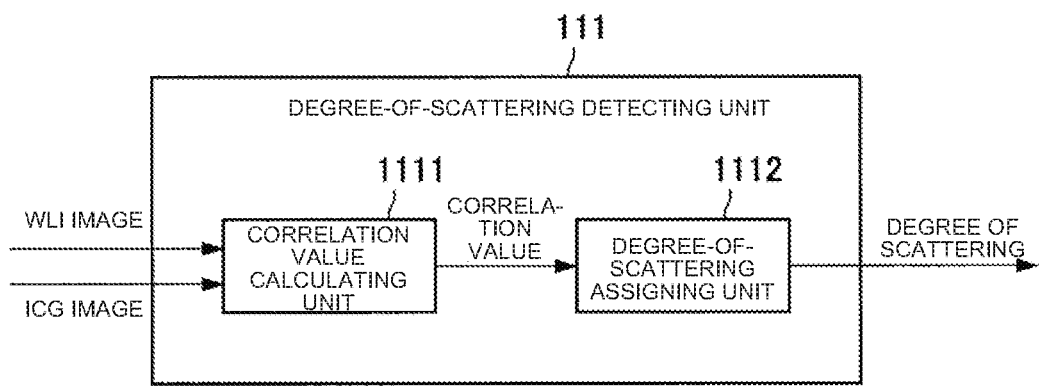
FIG. 5 is a diagram illustrating a detailed configuration example of a degree-of-scattering detecting unit.

The functions of the degree-of-scattering detecting unit 111 will be described in detail below. FIG. 5 is a diagram illustrating a detailed configuration example of the degree-of-scattering detecting unit 111. As illustrated in FIG. 5, the degree-of-scattering detecting unit 111 includes a correlation value calculating unit 1111 and a degree-of-scattering assigning unit 1112.

Here, the ICG image is obtained by capturing light that has transmitted through a living body. Accordingly, a degree of blurring of the ICG image due to light scattering is likely to increase as compared to the WLI image. Therefore, it is assumed that the degree of blurring of the ICG image due to light scattering increases with a decrease in a correlation value between the ICG image and the WLI image. In view of this, the degree-of-scattering detecting unit 111 causes the correlation value calculating unit 1111 to calculate the correlation value between the ICG image and the WLI image using, and causes the degree-of-scattering assigning unit 1112 to determine a degree of scattering on the basis of the correlation value (assign the degree of scattering to the correlation value).

More specifically, the correlation value calculating unit 1111 calculates the correlation value between the ICG image and the WLI image for each of regions (for example, for each of pixels or each of blocks). As a method of calculating the correlation value, any method may be adopted as long as it is possible to measure a degree of correlation between two data arrays. For example, it may be possible to use a normalized cross-correlation method as the method of calculating the correlation value. Examples of the normalized cross-correlation method include normalized cross-correlation (NCC) and zero-mean normalized cross-correlation (ZNCC).

Alternatively, the correlation value calculating unit 1111 may measure a frequency characteristic of each of the ICG image and the WLI image, and calculate a difference between the frequency characteristics of the ICG image and the WLI image as the correlation value.

The degree-of-scattering assigning unit 1112 determines the degree of scattering on the basis of the correlation value between the ICG image and the WLI image (assigns the degree of scattering to the correlation value). As described above, it is assumed that the degree of blurring of the ICG image due to light scattering increases with a decrease in the correlation value between the ICG image and the WLI image. Therefore, the degree-of-scattering assigning unit 1112 may determine a larger degree of scattering for a smaller absolute value of the correlation value (assign a large degree of scattering to the correlation value with a small absolute value).

FIG. 6 is a diagram illustrating an example of a correspondence relationship between the correlation value and the degree of scattering. FIG. 6 illustrates a correspondence table 1113 that contains the absolute value of the correlation value and the degree of scattering. As for the degree of scattering, a larger value indicates a larger degree of scattering. As illustrated in FIG. 6, the degree-of-scattering assigning unit 1112 may determine a larger degree of scattering increases for a smaller absolute value of the correlation value (assign a large degree of scattering to the correlation value with a small absolute value). However, the correspondence relationship between the correlation value and the degree of scattering is not limited to the example as illustrated in FIG. 6.

Meanwhile, in the first embodiment of the present disclosure, it is mainly assumed that the object feature includes the degree of scattering. In other words, it is mainly assumed that the object feature detecting unit 110 detects the degree of scattering. However, the object feature may include the correlation value itself instead of the degree of scattering. In other words, the object feature detecting unit 110 need not detect the degree of scattering. In this case, the degree-of-scattering detecting unit 111 need not include the degree-of-scattering assigning unit 1112.

Further, it may be possible to use a difference value between the ICG image and the WLI image instead of the correlation value between the ICG image and the WLI image. In this case, it is assumed that the degree of blurring of the ICG image due to light scattering increases with an increase in the difference value between the ICG image and the WLI image. Therefore, the degree-of-scattering assigning unit 1112 may determine a larger degree of scattering for a larger absolute value of the difference value (assign a large degree of scattering to the difference value with a large absolute value).

Thus, the details of the functions of the degree-of-scattering detecting unit 111 have been described above.

(Vascular Diameter Detecting Unit 112)

Figure 7:
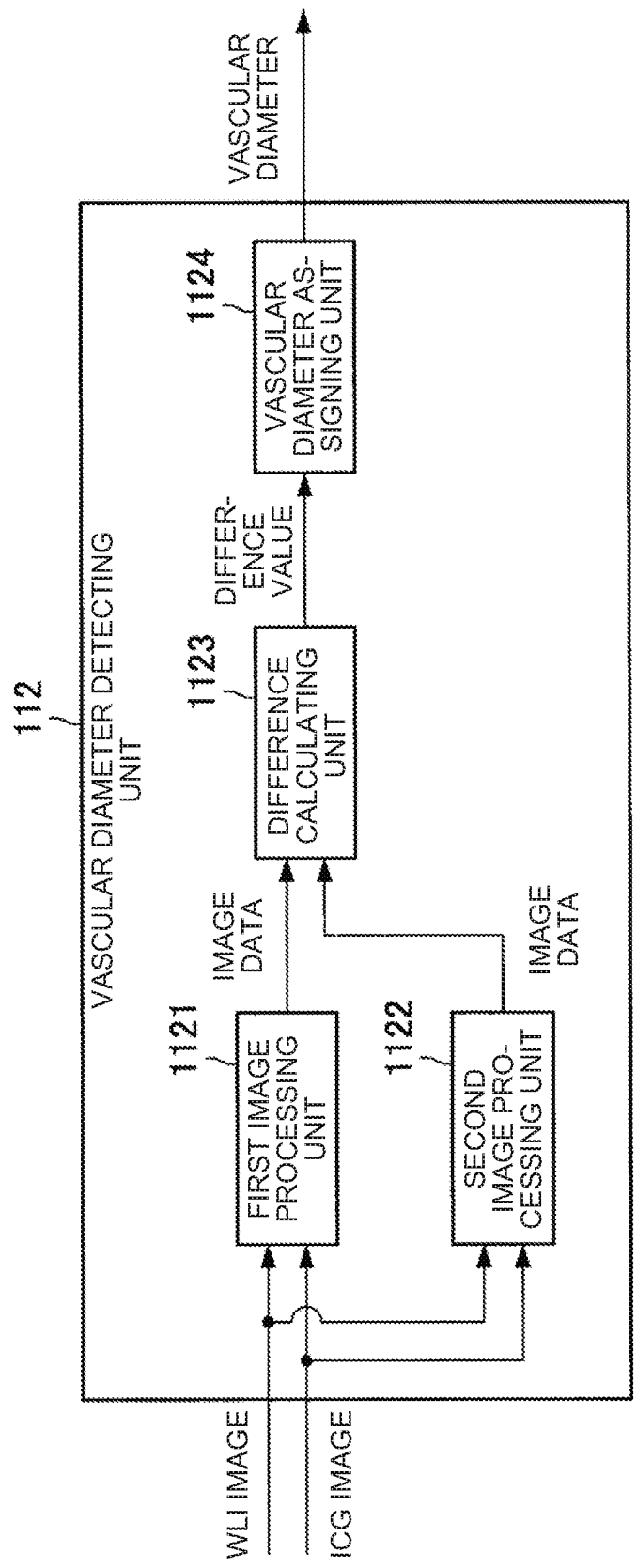
FIG. 7 is a diagram illustrating a detailed configuration example of a vascular diameter detecting unit.

Functions of the vascular diameter detecting unit 112 will be described in detail below. FIG. 7 is a diagram illustrating a detailed configuration example of the vascular diameter detecting unit 112. As illustrated in FIG. 7, the vascular diameter detecting unit 112 includes a first image processing unit 1121, a second image processing unit 1122, a difference calculating unit 1123, and a vascular diameter assigning unit 1124.

Here, if image processing is performed on the ICG image at different intensities, a difference between blood vessels that appear in two processing results tends to increase with a decrease in the vascular diameter. This tendency will be described with reference to FIG. 8. Meanwhile, in the first embodiment of the present disclosure, it is mainly assumed that image processing is performed on the ICG image. However, it may be possible to perform image processing on the WLI image, instead of the ICG image or together with the ICG image.

Figure 8:
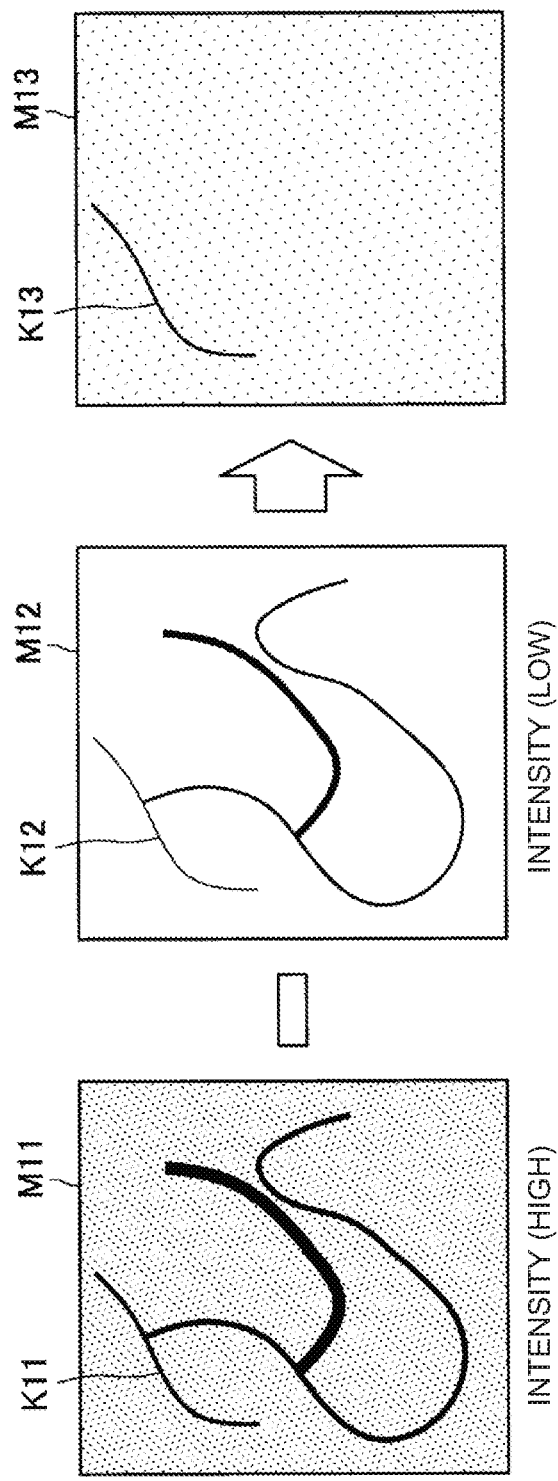
FIG. 8 is a diagram for explaining a case in which image processing is performed on ICG images at different intensities.

FIG. 8 is a diagram for explaining a case in which image processing is performed on the ICG image at different intensities. In the example illustrated in FIG. 8, it is mainly assumed that the enhancement process (for example, an unsharp masking process or the like) is performed on the ICG image. However, the image processing performed on the ICG image is not limited to the enhancement process. For example, the image processing performed on the ICG image may be a smoothing process (for example, a Gaussian filtering process or the like). In other words, the image processing performed on the ICG image may be any image processing by which a difference between blood vessels that appear in two processing results increases with a decrease in the vascular diameter.

FIG. 8 illustrates an ICG image M11 that is subjected to the enhancement process at a high intensity and an ICG image M12 that is subjected to the enhancement process at a low intensity. A thin blood vessel K11 and other blood vessels (a blood vessel with a medium thickness and a thick blood vessel) appear in the ICG image M11 that is subjected to the enhancement process at the high intensity, and a blood vessel K12 corresponding to the thin blood vessel K11 and other blood vessels (a blood vessel with a medium thickness and a thick blood vessel) appear in the ICG image M12 that is subjected to the enhancement process at the low intensity.

In this case, in a difference image M13 of the ICG image M11 that is subjected to the enhancement process at the high intensity and the ICG image M12 that is subjected to the enhancement process at the low intensity, only the thin blood vessel K11 appears and the other blood vessels (the blood vessel with a medium thickness and the thick blood vessel) do not appear. This phenomenon occurs due to the tendency to increase the difference between the blood vessels that appear in the two processing results with a decrease in the vascular diameter as described above.

Therefore, the first image processing unit 1121 performs image processing on the ICG image at a first intensity. Then, the second image processing unit 1122 performs image processing on the ICG image at a second intensity that is different from the first intensity. The difference calculating unit 1123 calculates a difference value between a processing result obtained by the first image processing unit 1121 and a processing result obtained by the second image processing unit 1122.

The vascular diameter assigning unit 1124 determines the vascular diameter on the basis of the difference value between the processing results obtained by performing the image processing on the ICG image at two different intensities (assigns the vascular diameter to the difference value). As described above, it is assumed that the vascular diameter decreases with an increase in the difference value between the processing results of the two kinds of image processing. Therefore, the vascular diameter assigning unit 1124 may determine a smaller vascular diameter for a larger difference value between the processing results of the two kinds of image processing (assign a small blood vessel diameter to the difference value).

Figures 9, 10:
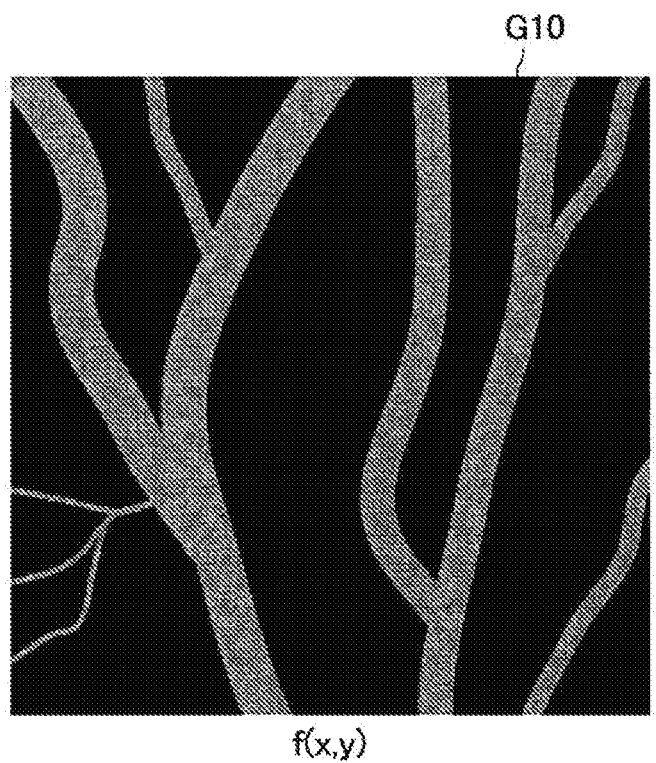
FIG. 9 is a diagram illustrating an example of a correspondence relationship between a difference value and a vascular diameter.
FIG. 10 is a diagram illustrating an example of an ICG image.

FIG. 9 is a diagram illustrating an example of a correspondence relationship between the difference value and the vascular diameter. FIG. 9 illustrates a correspondence table 1125 that contains an absolute value of the difference value and the vascular diameter. As for the vascular diameter, a larger value indicates a smaller vascular diameter. As illustrated in FIG. 9, the vascular diameter assigning unit 1124 may determine a smaller vascular diameter decreases (a vascular diameter with a larger value) for a larger absolute value of the difference value. However, the correspondence relationship between the difference value and the vascular diameter is not limited to the example as illustrated in FIG. 9.

Meanwhile, in the first embodiment of the present disclosure, it is mainly assumed that the object feature includes the vascular diameter. In other words, it is mainly assumed that the object feature detecting unit 110 detects the vascular diameter. However, the object feature may include the difference value itself instead of the vascular diameter. In other words, the object feature detecting unit 110 need not detect the vascular diameter. In this case, the vascular diameter detecting unit 112 need not include the vascular diameter assigning unit 1124.

(Modification of Vascular Diameter Detecting Unit 112)

A modification of the vascular diameter detecting unit 112 will be described below. The vascular diameter detecting unit 112 may determine the vascular diameter by a different method. Specifically, the vascular diameter detecting unit 112 may determine the vascular diameter on the basis of an eigenvalue of a Hessian matrix that is calculated from the ICG image. In the following, the modification will be described. For details of the method, it is possible to refer to a reference literature of "A. F. Frangi et. al., "Multiscale vessel enhancement filtering", Proceedings of MICCAI, pp 130-137, 1998.".

FIG. 10 is a diagram illustrating an example of the ICG image. FIG. 10 illustrates an ICG image G10 that is input to the vascular diameter detecting unit 112. The vascular diameter detecting unit 112 calculates a Hessian matrix of the ICG image G10 for each of pixels. Here, the Hessian matrix for each of the pixels is represented by Expression 1 below, where (x, y) represents a coordinate of a pixel, and I represents a pixel value.

$$H = \begin{bmatrix} \frac{\partial^2 I}{\partial x^2} & \frac{\partial^2 I}{\partial x \partial y} \\ \frac{\partial^2 I}{\partial x \partial y} & \frac{\partial^2 I}{\partial y^2} \end{bmatrix} \quad (1)$$

Subsequently, the vascular diameter detecting unit 112 calculates an eigenvalue of the Hessian matrix for each of the pixels. The eigenvalue is represented by Expression 2 below.

$$\text{EIGENVALUE}(\lambda_1, \lambda_2) \text{ WHERE, } \lambda_1 \le \lambda_2 \quad (2)$$

The vascular diameter detecting unit 112 extracts blood vessels on the basis of a structure-based index RB and an intensity-based index S by using the eigenvalue. The structure-based index RB and the intensity-based index S are represented by Expression 3 below.

$$R_B = \left| \frac{\lambda_1}{\lambda_2} \right| \quad (3)$$

$$S = \|H\| = \sqrt{\sum_{i \le 2} \lambda_i^2}$$

Specifically, the vascular diameter detecting unit 112 extracts blood vessels using an Expression for blood vessel extraction using the structure-based index RB and the intensity-based index S. The expression for blood vessel extraction is represented by Expression 4 below using the structure-based index RB and the intensity-based index S.

$$V(s) = \exp\left[-\frac{R_B^2}{2\beta}\right] \cdot \left(1 - \exp\left[-\frac{S^2}{2c^2}\right]\right) \quad (4)$$

Here, the structure-based index RB decreases and a value of V(s) increases with an increase in a difference between two eigenvalues, so that a correspondence pixel is likely to be determined as a blood vessel. In contrast, the intensity-based index S decreases and the value of V(s) decreases at a pixel for which a change of the pixel value is small (a pixel in a background portion or the like), so that the pixel is likely to be determined as not being a blood vessel.

A more detailed example will be described below. As described above, the vascular diameter detecting unit 112 calculates the Hessian matrix of the ICG image G10 for each of the pixels. Here, a Hessian matrix H for each of the pixels is represented by Expression 5 below, where (x, y) represents a coordinate of a pixel.

$$H = \begin{bmatrix} G_{xx} & G_{xy} \\ G_{xy} & G_{yy} \end{bmatrix} \quad (5)$$

$$G_{xx} = -\frac{x^2 - \sigma^2}{2\pi\sigma^6} \exp\left(-\frac{x^2 + y^2}{2\sigma^2}\right)$$

$$G_{xy} = -\frac{xy}{2\pi\sigma^6} \exp\left(-\frac{x^2 + y^2}{2\sigma^2}\right)$$

$$G_{yy} = -\frac{y^2 - \sigma^2}{2\pi\sigma^6} \exp\left(-\frac{x^2 + y^2}{2\sigma^2}\right)$$

σ: SCALE OF GAUSSIAN FUNCTION

The vascular diameter detecting unit 112 calculates the eigenvalue as described above by using the Hessian matrix H for each of the pixels represented as above, and extracts blood vessels by using the expression for blood vessel extraction. More specifically, at a scale at which a certain pixel has a maximum pixel value among all of scales (at a scale at which V(s) has a maximum value), the vascular diameter detecting unit 112 determines this pixel as a blood vessel portion, and extracts a blood vessel at each of the scales. With this configuration, it becomes possible to extract a blood vessel for each size of the vascular diameter (it becomes possible to extract a blood vessel by taking into account a magnitude of the vascular diameter).

Figure 11:
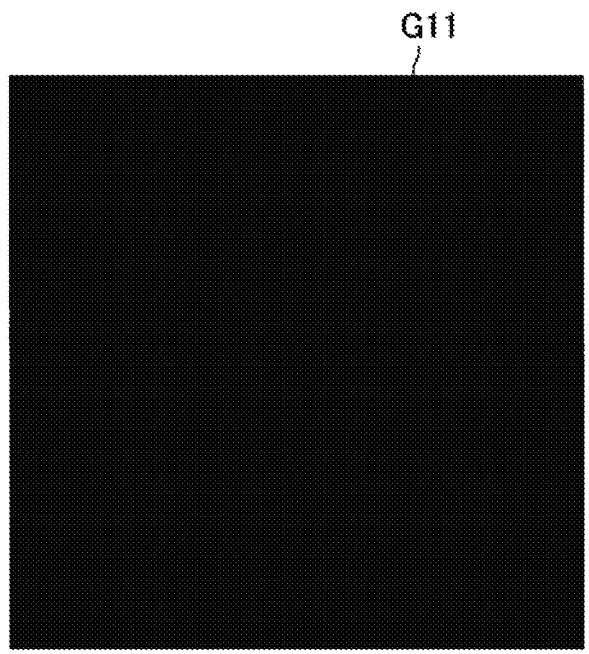
FIG. 11 is a diagram illustrating an example of an ICG image at a scale "0.5".
Figure 12:
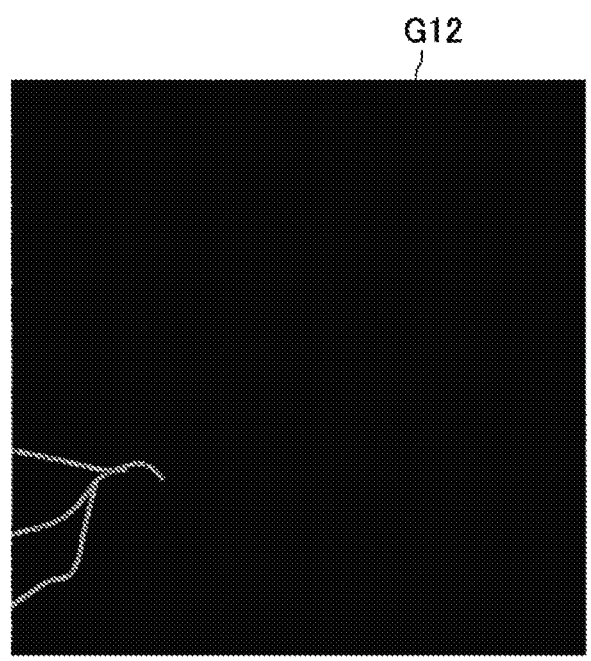
FIG. 12 is a diagram illustrating an example of an ICG image at a scale "5".
Figure 13:
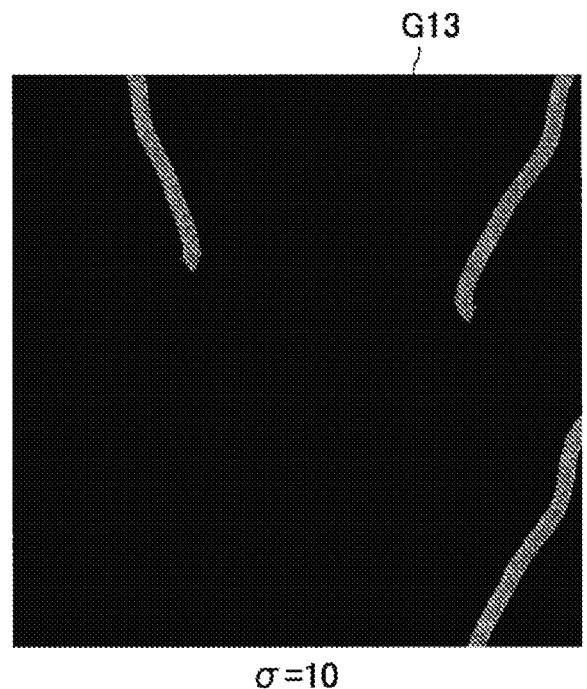
FIG. 13 is a diagram illustrating an example of an ICG image at a scale "10".
Figure 14:
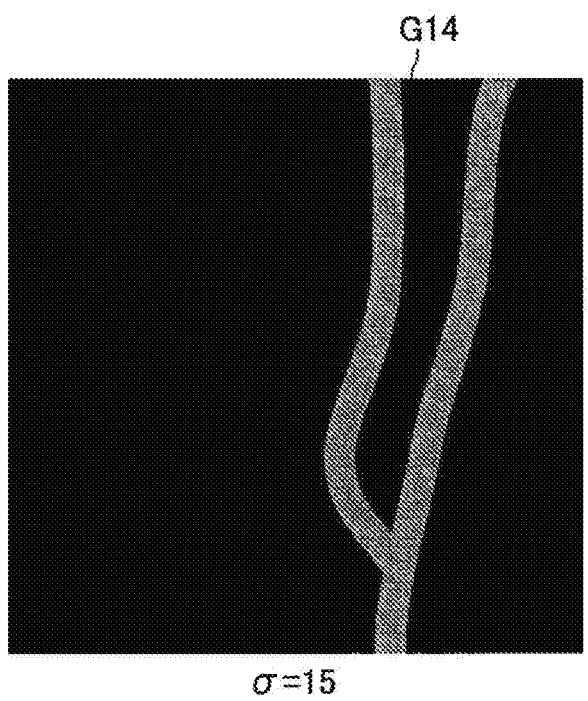
FIG. 14 is a diagram illustrating an example of an ICG image at a scale "15".
Figure 15:
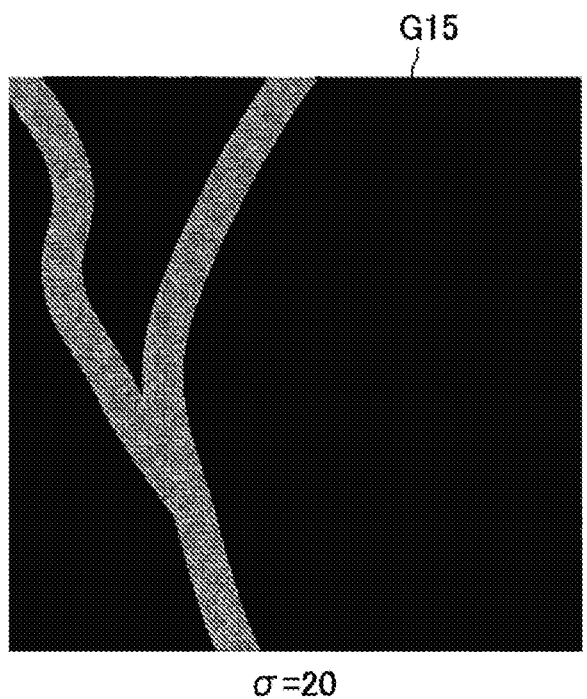
FIG. 15 is a diagram illustrating an example of an ICG image at a scale "20".

FIG. 11 to FIG. 15 are diagrams illustrating examples of ICG images at different scales. FIG. 11 illustrates an ICG image G11 at a scale of "0.5". FIG. 12 illustrates an ICG image G12 at a scale of "5". FIG. 13 illustrates an ICG image G13 at a scale of "10". FIG. 14 illustrates an ICG image G14 at a scale of "15". FIG. 15 illustrates an ICG image G15 at a scale of "20". With reference to FIG. 11 to FIG. 15, it is possible to recognize that a thicker blood vessel is extracted with an increase in the scale.

Thus, the details of the functions of the vascular diameter detecting unit 112 have been described above.

(Vascular Density Detecting Unit 113)

Figure 16:
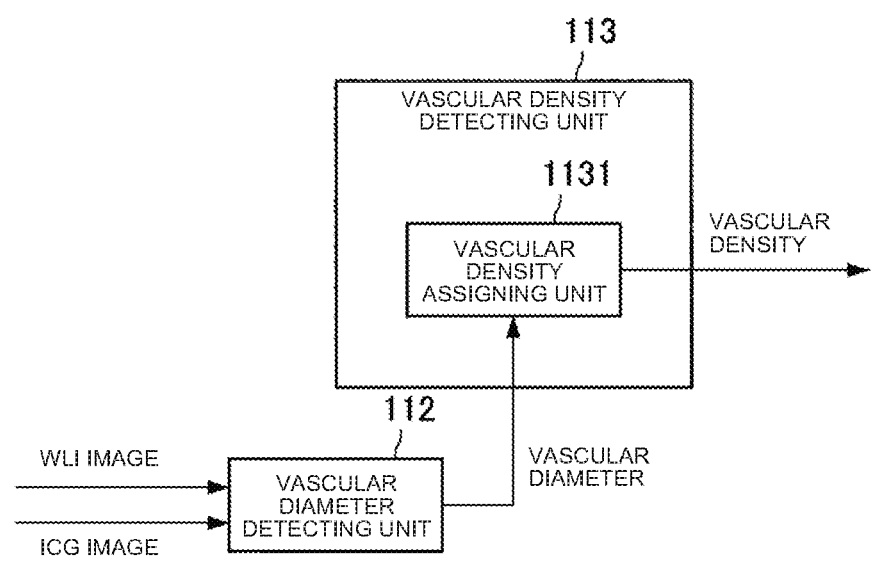
FIG. 16 is a diagram illustrating a detailed configuration example of a vascular density detecting unit.

Functions of the vascular density detecting unit 113 will be described in detail below. FIG. 16 is a diagram illustrating a detailed configuration example of the vascular density detecting unit 113. As illustrated in FIG. 16, the vascular density detecting unit 113 includes a vascular density assigning unit 1131. Meanwhile, as illustrated in FIG. 16, information on the vascular diameter detected by the vascular diameter detecting unit 112 may be input to the vascular density detecting unit 113.

The vascular density assigning unit 1131 determines a vascular density based on the ICG image. In the following, it is mainly assumed that the vascular density is a combination of a ratio of an area of blood vessels in a certain area of the ICG image (hereinafter, also referred to as a "blood vessel ratio") and a vascular diameter that most frequently appears in the area (hereinafter, also referred to as a "most-frequent vascular diameter"). However, the vascular density may be determined by any method. For example, the vascular density may be the number of blood vessels that are present in a certain area of the ICG image (hereinafter, also simply referred to as a "blood vessel number") or a ratio of blood vessels.

Figures 17, 18:
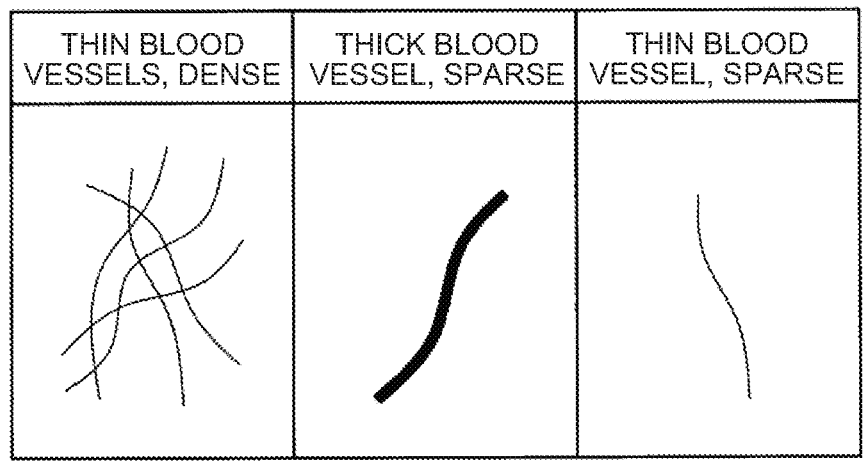
FIG. 17 is a diagram for explaining a vascular density.
FIG. 18 is a diagram illustrating an example of a correspondence relationship between a combination of a ratio of blood vessels and a vascular diameter that most frequently appears and a vascular density.

FIG. 17 is a diagram for explaining the vascular density. FIG. 17 illustrates a case in which thin blood vessels are present densely, a case in which a thick blood vessel is present sparsely, and a case in which a thin blood vessel is present sparsely. In the example illustrated in FIG. 17, the case in which the thick blood vessel is present sparsely has a higher vascular density than the case in which the thin blood vessel is present sparsely (the vascular density increases with an increase in the ratio of blood vessels). Further, a ratio (area) of blood vessels in a certain area of the ICG image is approximately the same between the case in which the thin blood vessels are present densely and the case in which the thin blood vessel is present sparsely, but the vascular density is higher in a case in which the most-frequent vascular diameter is thin than in the case in which the most-frequent vascular diameter is thick.

The vascular density assigning unit 1131 determines the vascular density on the basis of a combination of the ratio of blood vessels and the most-frequent vascular diameter (assigns the vascular density to the combination). As described above, it is assumed that the vascular density increases with an increase in the ratio of blood vessels. Further, it is assumed that the vascular density increases with a decrease in the most-frequent vascular diameter. Therefore, the vascular density assigning unit 1131 may determine a higher vascular density for a larger ratio of blood vessels or for a smaller most-frequent vascular diameter (assign a high vascular density to the combination of the ratio of blood vessels and the most-frequent vascular diameter).

FIG. 18 is a diagram illustrating an example of a correspondence relationship between the combination of the ratio of blood vessels and the most-frequent vascular diameter and the vascular density. FIG. 18 illustrates a correspondence table 1132 that contains the combination of the ratio of blood vessels and the most-frequent vascular diameter and the vascular density. Here, as for the vascular density, a larger value indicates a higher vascular density. As illustrated in FIG. 18, the vascular density assigning unit 1131 may determine a higher vascular density for a larger ratio of blood vessels or for a smaller most-frequent vascular diameter (assign a high vascular density to a combination of the ratio of blood vessels and the most-frequent vascular diameter). However, the correspondence relationship between the combination of the ratio of blood vessels and the most-frequent vascular diameter is not limited to the example as illustrated in FIG. 18.

Meanwhile, as described above, the vascular density may be the number of blood vessels or the ratio of blood vessels. In this case, the vascular density assigning unit 1131 may determine a higher vascular density for a larger number of blood vessels (assign a high vascular density to the number of blood vessels). Alternatively, the vascular density assigning unit 1131 may determine a higher vascular density for a larger ratio of blood vessels (assign a high vascular density to the ratio of blood vessels).

(Vascular Depth Detecting Unit 114)

Figures 19, 20:
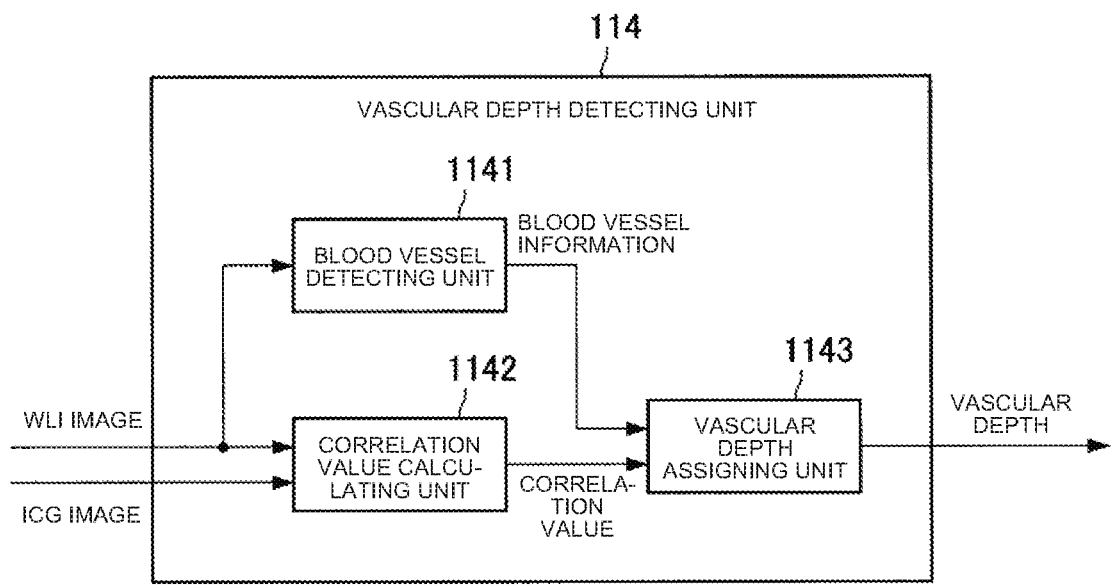
FIG. 19 is a diagram illustrating a detailed configuration example of a vascular depth detecting unit.
FIG. 20 is a diagram illustrating an example of a correspondence relationship between a combination of blood vessel information and a correlation value and a vascular depth.

Functions of the vascular depth detecting unit 114 will be described in detail below. FIG. 19 is a diagram illustrating a detailed configuration example of the vascular depth detecting unit 114. As illustrated in FIG. 19, the vascular depth detecting unit 114 includes a blood vessel detecting unit 1141, a correlation value calculating unit 1142, and a vascular depth assigning unit 1143. Meanwhile, the correlation value calculating unit 1142 may function similarly to the correlation value calculating unit 1111 of the degree-of-scattering detecting unit 111.

Here, it is assumed that a blood vessel appears more clearly in the ICG image than the WLI image such that a blood vessel does not appear in the WLI image but a blood vessel appears in the ICG image. In this case, it is assumed that the blood vessel is present at a deep position in a living body. Therefore, it is assumed that a vascular depth increases with a decrease in the correlation value between the ICG image and the WLI image. Further, if a blood vessel is not detected, it is assumed that a vascular depth is larger as compared to a case in which a blood vessel is detected.

Therefore, the vascular depth detecting unit 114 causes the blood vessel detecting unit 1141 to detect whether a blood vessel is present in at least one of the ICG image and the WLI image, causes the correlation value calculating unit 1142 to calculate the correlation value between the ICG image and the WLI image, and causes the vascular depth assigning unit 1143 to determine a degree of scattering on the basis of information indicating whether a blood vessel is present (hereinafter, also referred to as "blood vessel information") and the correlation value (assign the vascular depth to the blood vessel information and the correlation value).

More specifically, the blood vessel detecting unit 1141 detects whether a blood vessel is present in at least one of the ICG image and the WLI image (in the ICG image, in the WLI image, or in both of the ICG image and the WLI image) for each of regions (for example, for each of pixels or for each of blocks). In this case, it is sufficient that the blood vessel detecting unit 1141 calculates color information or a signal band, and detects whether a blood vessel is present on the basis of the color information or the signal band.

The vascular depth assigning unit 1143 determines the degree of scattering on the basis of the blood vessel information and the correlation value (assigns the vascular depth to the blood vessel information and the correlation value). As described above, it is assumed that the vascular depth increases with a decrease in the correlation value between the ICG image and the WLI image. Therefore, the degree-of-scattering assigning unit 1112 may determine a larger vascular depth for a smaller absolute value of the correlation value (assign a large vascular depth to the correlation value with a small absolute value).

Furthermore, as described above, if a blood vessel is not detected, it is assumed that the vascular depth is larger as compared to the case in which a blood vessel is detected. Therefore, if a blood vessel is not detected, the vascular depth assigning unit 1143 may determine a larger vascular depth as compared to the case in which a blood vessel is detected (if a blood vessel is not detected, a larger vascular depth is assigned as compared to the case in which a blood vessel is detected).

FIG. 20 is a diagram illustrating an example of a correspondence relationship between a combination of the blood vessel information and the correlation value and the vascular depth. FIG. 20 illustrates a correspondence table 1144 that contains the combination of the blood vessel information and the correlation value and the vascular depth. As for the vascular depth, a larger value indicates a deeper position at which a blood vessel is present in a living body. As illustrated in FIG. 20, if a blood vessel is not detected, the vascular depth assigning unit 1143 may determine a larger vascular depth as compared to the case in which a blood vessel is detected, and may determine a larger vascular depth for a smaller absolute value of the correlation value. However, the correspondence relationship between the combination of the blood vessel information and the correlation value and the vascular depth is not limited to the example as illustrated in FIG. 20.

Further, it may be possible to use a difference value between the ICG image and the WLI image instead of the correlation value between the ICG image and the WLI image. In this case, it is assumed that the vascular depth increases with an increase in the difference value between the ICG image and the WLI image. Therefore, the vascular depth assigning unit 1143 may determine a larger vascular depth for a larger absolute value of the difference value (assign a large vascular depth to the difference value with a large absolute value).

Thus, the details of the functions of the vascular depth detecting unit 114 have been described above.

(Enhancement Processing Unit 160)

Figure 21:
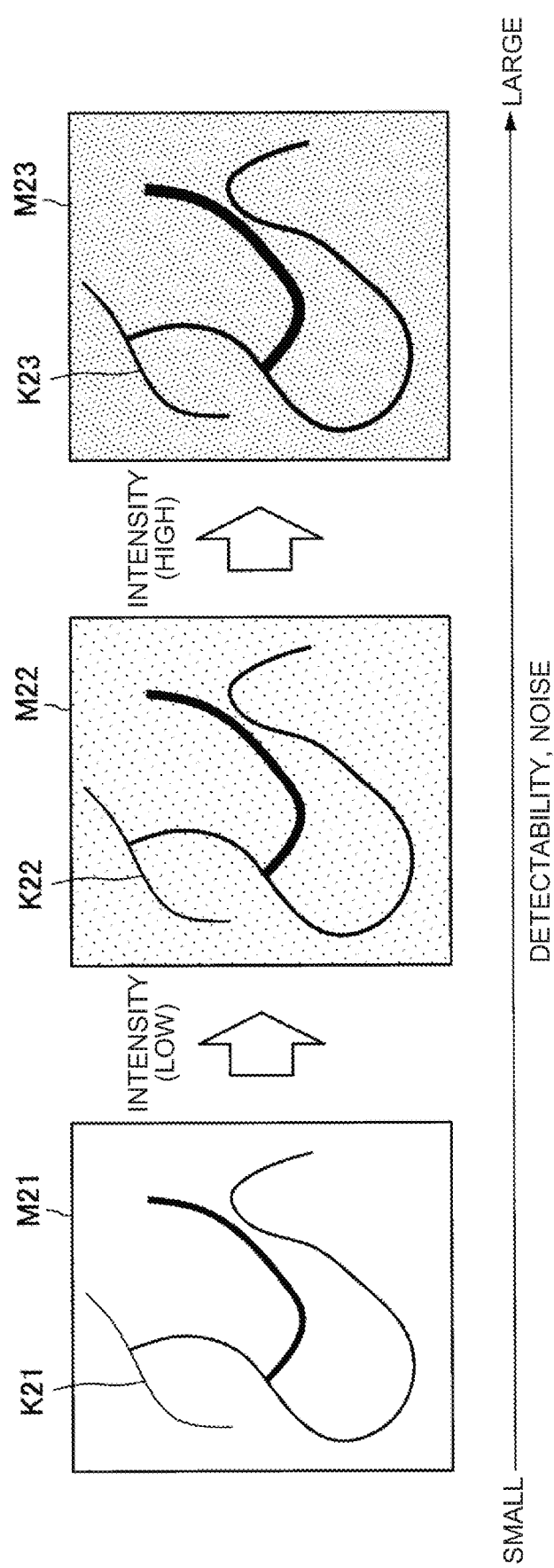
FIG. 21 is a diagram for explaining a case in which a degree of an enhancement process is uniform over the entire ICG image.

Functions of the enhancement processing unit 160 will be described in detail below. Here, a case will be described in which the degree of the enhancement process is uniform over the entire ICG image. FIG. 21 is a diagram for explaining the case in which the degree of the enhancement process is uniform over the entire ICG image. FIG. 21 illustrates an ICG image M21 before being subjected to the enhancement process, an ICG image M22 that is subjected to the enhancement process at a low intensity, and an ICG image M23 that is subjected to the enhancement process at a high intensity.

Here, in the ICG image M21 before being subjected to the enhancement process, a thin blood vessel K21 remains thin and is not easily viewable. In contrast, in the ICG image M22 that is subjected to the enhancement process at the low intensity, a thickness of a thin blood vessel K22 is slightly increased, so that visibility of the thin blood vessel K22 is slightly improved. Further, in the ICG image M23 subjected to the enhancement process at the high intensity, a thickness of a thin blood vessel K23 is further increased, so that visibility of the thin blood vessel K23 is largely improved. However, it is recognized that noise in the entire image increases with an increase in the degree of the enhancement process.

Therefore, the enhancement processing unit 160 controls the degree of the enhancement process in accordance with the object feature detected by the object feature detecting unit 110. Specifically, it is sufficient that the enhancement processing unit 160 increases the degree of the enhancement process with an increase in an object feature amount detected by the object feature detecting unit 110. With this configuration, the enhancement process is performed at a high intensity on a region that needs to be largely enhanced, and the enhancement process is performed at a low intensity on a region in which excessive enhancement needs to be avoided to reduce noise; therefore, the visibility can be improved.

Specifically, if the degree-of-scattering detecting unit 111 detects the degree of scattering, the enhancement processing unit 160 may increase the degree of the enhancement process with an increase in the degree of scattering. Further, if the degree-of-scattering detecting unit 111 detects the correlation value, the enhancement processing unit 160 may increase the degree of the enhancement process with a decrease in the correlation value. With this configuration, the degree of the enhancement process performed on a region in which fluorescence scattering is large is increased, and the degree of the enhancement process performed on other regions is reduced, so that the visibility is improved.

Further, if the vascular diameter detecting unit 112 detects the vascular diameter, the enhancement processing unit 160 may increase the degree of the enhancement process with a decrease in the vascular diameter. Furthermore, if the vascular diameter detecting unit 112 detects the difference value between the ICG image and the WLI image, the enhancement processing unit 160 may increase the degree of the enhancement process with a decrease in the absolute value of the difference value. With this configuration, the degree of the enhancement process performed on a region in which the vascular diameter is small is increased, and the degree of the enhancement process performed on other regions is reduced, so that the visibility is improved.

Figure 22:
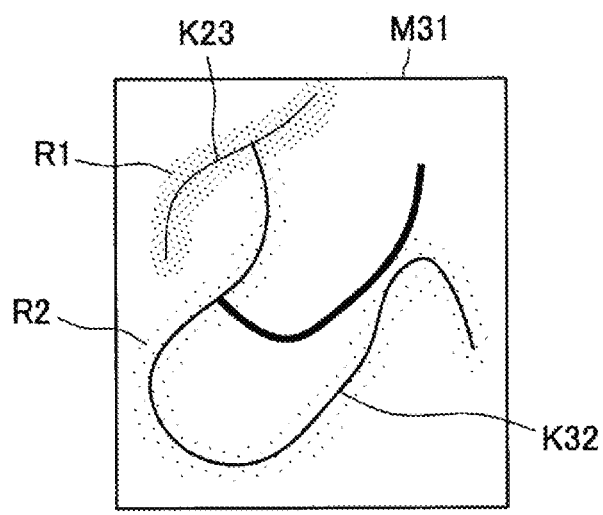
FIG. 22 is a diagram illustrating an example of an ICG image on which enhancement processes are performed at different degrees in accordance with vascular diameters.

FIG. 22 is a diagram illustrating an example of an ICG image on which enhancement processes are performed at different intensities in accordance with vascular diameters. FIG. 22 illustrates an ICG image M31 on which enhancement processes are performed at different intensities in accordance with vascular diameters. An enhancement process at a high intensity is performed on a region R1 in which a blood vessel K23 with a small diameter is present. In contrast, an enhancement process at a low intensity is performed on a region R2 in which a blood vessel K32 with a large diameter is present. Through the enhancement processes as described above, visibility of the blood vessel K23 with the small diameter and the blood vessel K32 with the large diameter is improved.

Explanation will be continued with reference to FIG. 21. If the vascular density detecting unit 113 detects the vascular density, the enhancement processing unit 160 may increase the degree of the enhancement process with an increase in the vascular density. With this configuration, the degree of the enhancement process performed on a region with a high vascular density is increased, and the degree of the enhancement process performed on other regions is reduced, so that the visibility is improved.

Further, if the vascular depth detecting unit 114 detects the vascular depth, the enhancement processing unit 160 may increase the degree of the enhancement process with an increase in the vascular depth. With this configuration, the degree of the enhancement process performed on a region with a large vascular depth is increased, and the degree of the enhancement process performed on other regions is reduced, so that the visibility is improved.

While it is assumed that, in the first embodiment of the present disclosure, the enhancement process is performed on the ICG image, it may be possible to perform a noise removal process instead of the enhancement process on the ICG image.

In this case, the enhancement processing unit 160 controls a degree of noise removal in accordance with the object feature detected by the object feature detecting unit 110. Specifically, it is sufficient that the enhancement processing unit 160 increases the degree of the noise removal process with an increase in the object feature amount detected by the object feature detecting unit 110. With this configuration, the noise removal process is performed at a high intensity on a region in which noise needs to be removed intensively (region that is not easily viewable), and the noise removal process is performed at a low intensity on other regions, so that the visibility is improved.

Specifically, if the degree-of-scattering detecting unit 111 detects the degree of scattering, the degree of the noise removal process may be increased with an increase in the degree of scattering. Further, if the degree-of-scattering detecting unit 111 detects the correlation value, the degree of the noise removal process may be increased with a decrease in the correlation value. Furthermore, if the vascular diameter detecting unit 112 detects the vascular diameter, the degree of the noise removal process may be increased with a decrease in the vascular diameter. Moreover, if the vascular diameter detecting unit 112 detects the difference value between the ICG image and the WLI image, the degree of the noise removal process may be increased with a decrease in the absolute value of the difference value.

Furthermore, if the vascular density detecting unit 113 detects the vascular density, the degree of the noise removal process may be increased with an increase in the vascular density. Moreover, if the vascular depth detecting unit 114 detects the vascular depth, the degree of the enhancement process may be increased with an increase in the vascular depth.

Meanwhile, a specific method for implementing the enhancement process by the enhancement processing unit 160 is not specifically limited. For example, if it is assumed that a pixel value obtained before the enhancement process is performed on the ICG image is denoted by $x_0$, neighboring pixel values (including the pixel value $x_0$) used to the enhancement process on the pixel value $x_0$ are denoted by $x_0$ to $x_n$, and the degree of enhancement is denoted by p, a pixel value y obtained after the enhancement process is performed on the ICG image is represented by Expression 6 below.

$$y = x_0 + p\left(\sum_{i=0}^{n} x_i - x_0\right) \qquad (6)$$

Thus, the first embodiment of the present disclosure has been described above.

4. Second Embodiment

A second embodiment of the present disclosure will be described below.

(Functional Configuration Example of CCU)

Figure 23:
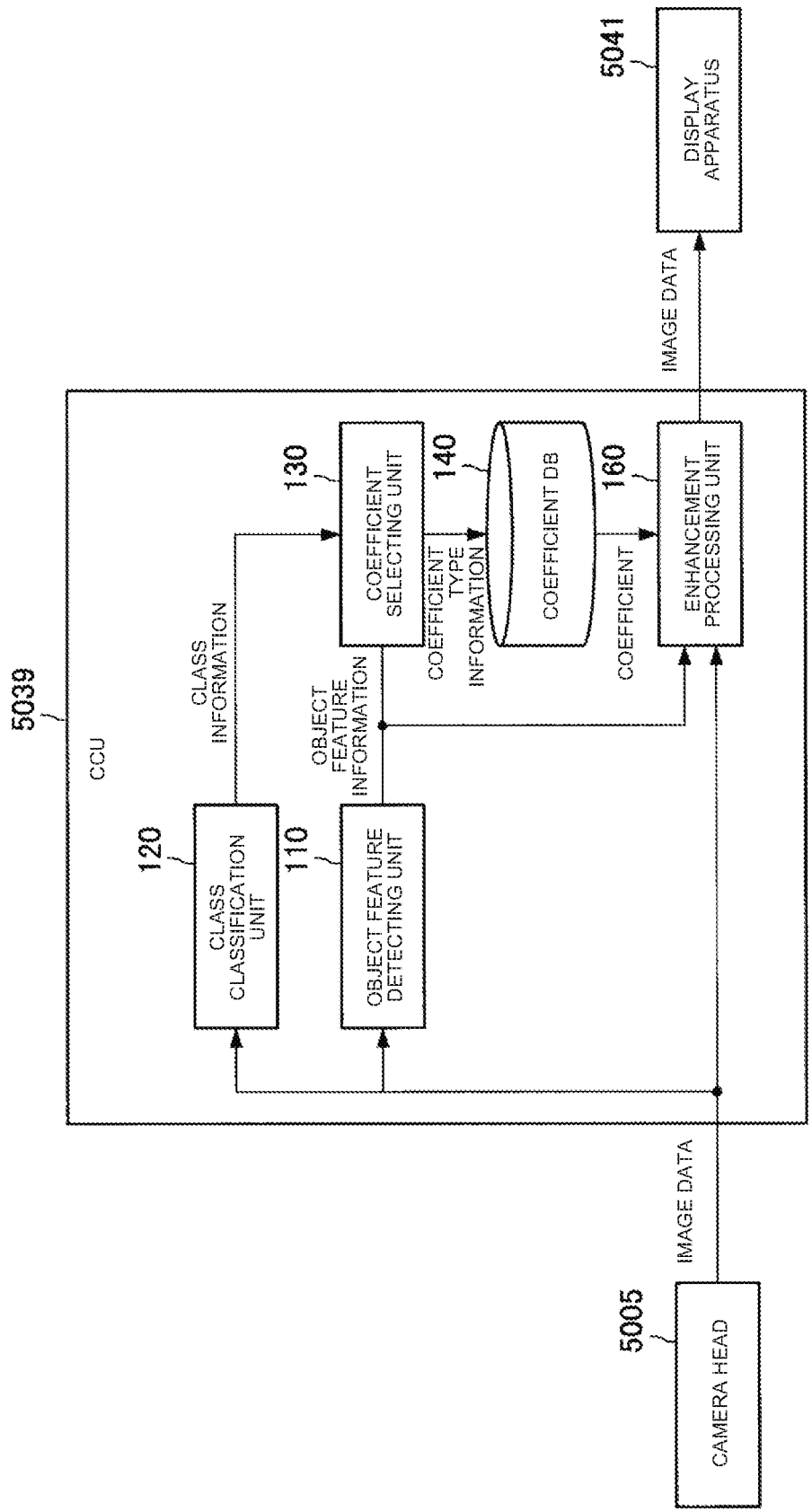
FIG. 23 is a diagram illustrating an example of an ICG image on which enhancement processes are performed at different intensities in accordance with vascular diameters.

First, a functional configuration example of a CCU according to the second embodiment of the present disclosure will be described. FIG. 23 is a block diagram illustrating the functional configuration example of the CCU according to the second embodiment of the present disclosure. As illustrated in FIG. 23, the CCU 5039 according to the second embodiment of the present disclosure includes, similarly to the first embodiment of the present disclosure, the object feature detecting unit 110 and the enhancement processing unit 160. The CCU 5039 according to the second embodiment of the present disclosure further includes a class classification unit 120, a coefficient selecting unit 130, and a coefficient database (DB) 140.

In the coefficient DB 140, a correspondence (hereinafter, also referred to as a "coefficient set") between the object feature and a coefficient of the enhancement process (hereinafter, also simply referred to as a "coefficient"), which is generated by machine learning using a past ICG image, is registered. More specifically, the correspondence between the object feature and the coefficient is established through a learning process on a plurality of combinations of an object feature detected from a past ICG image and a coefficient. In this manner, the coefficient is prepared in advance for each of classes of the object feature.

The class classification unit 120 determines which of the coefficient sets includes a feature that matches a part or the whole of the object feature detected by the object feature detecting unit 110, and determines a class to which the object feature belongs. The coefficient selecting unit 130 selects a coefficient corresponding to the class from the coefficient DB 140. Meanwhile, as types of the feature included in the coefficient set, various types may be adopted.

Specifically, as a first example, it is assumed that a coefficient corresponding to the object feature detected by the object feature detecting unit 110 is registered in the coefficient DB 140. As a second example, it is assumed that a coefficient corresponding to a part (a first feature) of the object feature detected by the object feature detecting unit 110 is registered in the coefficient DB 140, but a coefficient corresponding to the rest (a second feature different from the first feature) of the object feature detected by the object feature detecting unit 110 is not registered in the coefficient DB 140. As a third example, it is assumed that only a single coefficient is registered in the coefficient DB 140.

Figure 24:
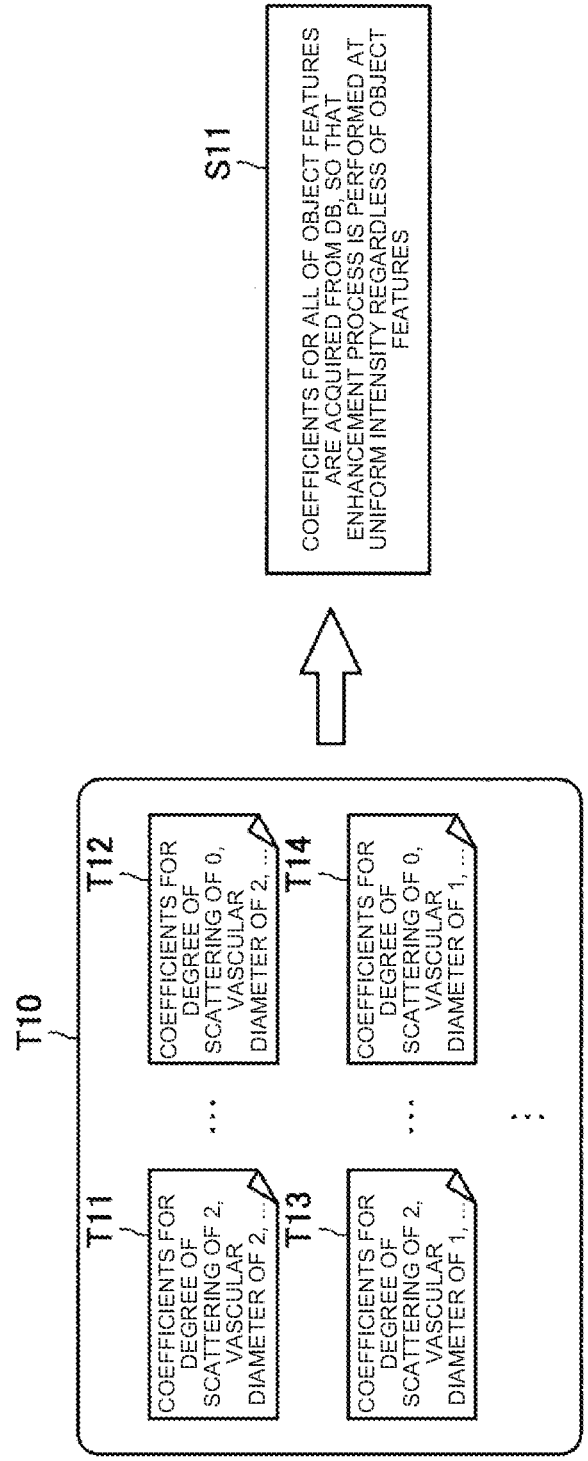
FIG. 24 is a diagram illustrating a case (first example) in which a coefficient corresponding to an object feature is registered in a coefficient DB.

FIG. 24 is a diagram illustrating a case in which the coefficient corresponding to the object feature is registered in the coefficient DB 140 (first example). As illustrated in FIG. 24, a coefficient set T10 includes coefficient sets T11 to T14 in each of which the object feature (the degree of scattering, the vascular diameter, and the like) detected by the object feature detecting unit 110 and a coefficient are associated.

In this manner, if the coefficient corresponding to the object feature detected by the object feature detecting unit 110 is registered in the coefficient DB 140, the coefficient corresponding to the whole object feature is acquired from the coefficient DB 140. Therefore, it is sufficient that the enhancement processing unit 160 controls the enhancement process in accordance with the coefficient. In other words, the enhancement process performed by the enhancement processing unit 160 may be uniform independently of the object feature detected by the object feature detecting unit 110 (S11).

Figure 25:
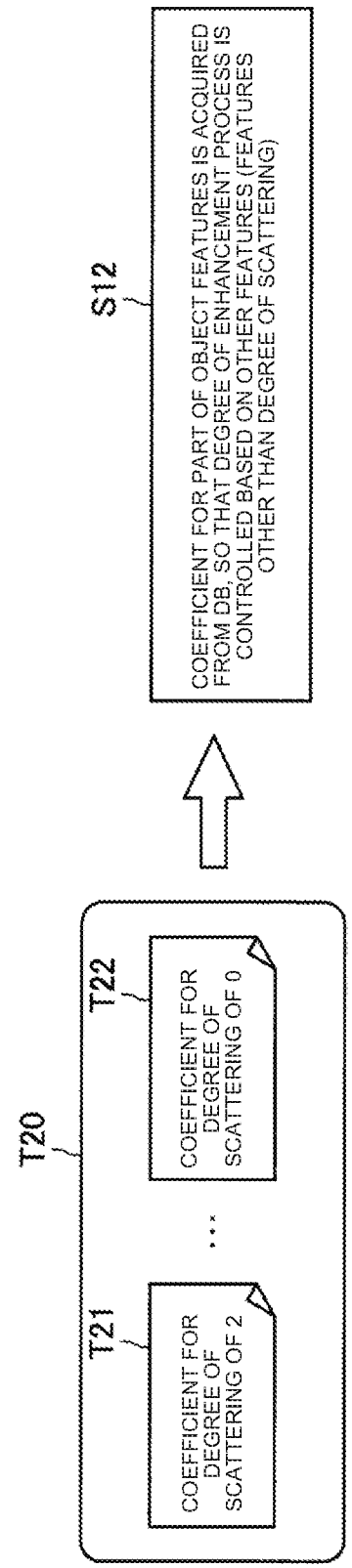
FIG. 25 is a diagram illustrating a case (second example) in which a coefficient corresponding to a part of the object feature is registered in the coefficient DB but a coefficient corresponding to the rest of the object feature is not registered in the coefficient DB.

FIG. 25 is a diagram illustrating a case (second example) in which the coefficient corresponding to the part (first feature) of the object feature is registered in the coefficient DB 140, but the coefficient corresponding to the rest (second feature) of the object feature is not registered in the coefficient DB 140. As illustrated in FIG. 25, a coefficient set T20 includes coefficient sets T21 to T22 in each of which the part (degree of scattering) of the object feature detected by the object feature detecting unit 110 and a coefficient are associated.

In this manner, if the coefficient corresponding to the part (first feature) of the object feature detected by the object feature detecting unit 110 is registered in the coefficient DB 140 but the coefficient corresponding to the rest (second feature) of the object feature is not registered in the coefficient DB 140, only the coefficient corresponding to the part of the object feature is acquired from the coefficient DB 140. Therefore, it is sufficient that the enhancement processing unit 160 controls the enhancement process in accordance with the coefficient, and controls the degree of the enhancement process on the basis of the rest (second feature) of the object feature detected by the object feature detecting unit 110. In other words, the degree of the enhancement process performed by the enhancement processing unit 160 may be controlled based on the other feature (feature other than the degree of scattering) (S12).

Figure 26:
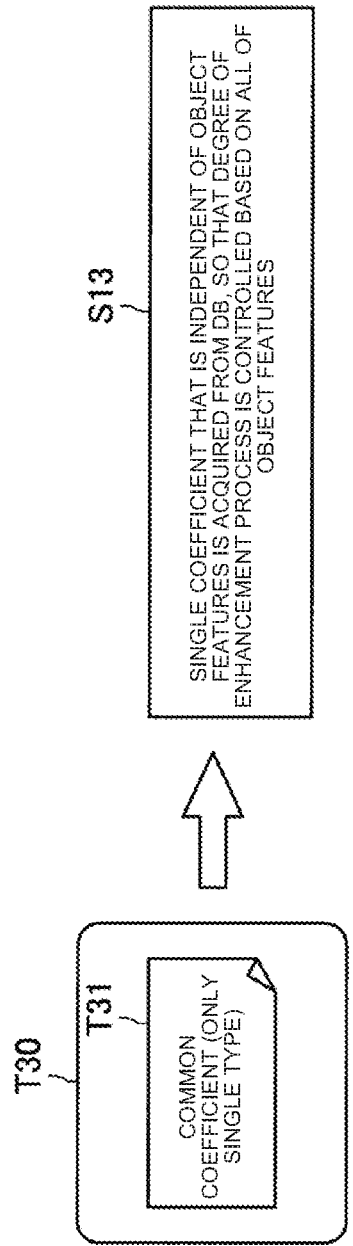
FIG. 26 is a diagram illustrating a case (third example) in which only a single coefficient is registered in the coefficient DB.

FIG. 26 is a diagram illustrating a case (third example) in which only a single coefficient is registered in the coefficient DB 140. As illustrated in FIG. 26, a coefficient set T30 includes a coefficient set T31 containing a single kind of coefficient. In this manner, if the single coefficient is registered in the coefficient DB 140, the single coefficient is acquired from the coefficient DB 140. Therefore, it is sufficient that the enhancement processing unit 160 controls the enhancement process in accordance with the single coefficient, and controls the degree of the enhancement process on the basis of the object feature detected by the object feature detecting unit 110. In other words, the degree of the enhancement process performed by the enhancement processing unit 160 may be controlled based on the whole object feature (S13).

Meanwhile, a specific method for implementing the enhancement process by the enhancement processing unit 160 according to the second embodiment of the present disclosure is not specifically limited. For example, similarly to the first embodiment of the present disclosure, if it is assumed that a pixel value obtained before the enhancement process is performed on the ICG image is denoted by $x_0$, neighboring pixel values (including the pixel value $x_0$) used to the enhancement process on the pixel value $x_0$ are denoted by $x_0$ to $x_n$, the degree of enhancement is denoted by p, and the coefficient of the second embodiment of the present disclosure is denoted by $a_i$, a pixel value y obtained after the enhancement process is performed on the ICG image is represented by Expression 7 below.

$$y = x_0 + p\left(\sum_{i=0}^{n} a_i x_i - x_0\right) \tag{7}$$

Thus, the second embodiment of the present disclosure has been described above.

5. Conclusion

As described above, according to the embodiments of the present disclosure, the CCU 5039 is provided as one example of the image processing apparatus, where the CCU 5039 includes the object feature detecting unit 110 that detects a feature of the ICG image that is one example of the first image data obtained by capturing an image of a blood vessel by the ICG fluorescence imaging, and the enhancement processing unit 160 that controls the degree of the enhancement process performed on the ICG image on the basis of the feature detected by the object feature detecting unit 110. With this configuration, it is possible to improve visibility of a fluorescence image. Further, with the improvement of the visibility of the fluorescence image, it becomes possible to assist diagnosis of an observation target.

While the preferred embodiments of the present disclosure have been described in detail above with reference to the accompanying drawings, the technical scope of the present disclosure is not limited to the examples as described above. It is obvious that a person skilled in the technical field of the present disclosure may conceive various alternations and modifications within the scope of the appended claims, and it should be understood that they will naturally come under the technical scope of the present disclosure.

For example, it may be possible to generate a program that causes hardware, such as a CPU, a ROM, and a RAM, incorporated in a computer to implement the same functions as the functions of the control unit 5063 as described above. Further, it may be possible to provide a computer-readable recording medium that stores therein the program.

Furthermore, the effects described in this specification are merely illustrative or exemplified effects, and are not limitative. That is, with or in the place of the above effects, the technology according to the present disclosure may achieve other effects that are clear to those skilled in the art from the description of this specification.

The following configurations are also within the technical scope of the present disclosure.

(1)

An image processing apparatus comprising:
a feature detecting unit configured to detect a feature of first image data that is obtained by capturing an image of a blood vessel by ICG fluorescence imaging; and
an enhancement processing unit configured to control a degree of an enhancement process performed on the first image data, on the basis of the feature.

(2)

The image processing apparatus according to (1), wherein the feature includes one of a correlation value between the first image data and second image data that is obtained by capturing an image of the blood vessel by applying white light and a degree of scattering that is determined based on the correlation value.

(3)

The image processing apparatus according to (2), wherein the enhancement processing unit increases a degree of the enhancement process with a decrease in the correlation value or with an increase in the degree of scattering.

(4)

The image processing apparatus according to any one of (1) to (3), wherein the feature includes one of a difference value between processing results of two kinds of image processing that are performed at different intensities on the first image data and a vascular diameter that is determined based on the difference value.

(5)

The image processing apparatus according to (4), wherein the enhancement processing unit increases the degree of the enhancement process with a decrease in an absolute value of the difference value or with a decrease in the vascular diameter.

(6)

The image processing apparatus according to any one of (1) to (3), wherein the feature includes a vascular diameter that is determined based on an eigenvalue of a Hessian matrix calculated from the first image data.

(7)

The image processing apparatus according to (6), wherein the enhancement processing unit increases the degree of the enhancement process with a decrease in the vascular diameter.

(8)

The image processing apparatus according to any one of (1) to (7), wherein the feature includes a vascular density that is determined based on the first image data.

(9)

The image processing apparatus according to (8), wherein the enhancement processing unit increases the degree of the enhancement process with an increase in the vascular density.

(10)

The image processing apparatus according to any one of (1) to (9), wherein the feature includes a correlation value between the first image data and second image data that is obtained by capturing an image of the blood vessel by applying white light and a vascular depth that is determined in accordance with information indicating whether a blood vessel is present in at least one of the first image data and the second image data.

(11)

The image processing apparatus according to (10), wherein the enhancement processing unit increases the degree of the enhancement process with an increase in the vascular depth.

(12)

The image processing apparatus according to any one of (1) to (11), wherein if a coefficient corresponding to the feature is registered, the enhancement processing unit controls the enhancement process in accordance with the coefficient.

(13)

The image processing apparatus according to any one of (1) to (11), wherein if a coefficient corresponding to a first feature is registered and a coefficient corresponding to a second feature that is different from the first feature is not registered, the enhancement processing unit controls the enhancement process in accordance with the coefficient and controls a degree of the enhancement process in accordance with the second feature.

(14)

The image processing apparatus according to any one of (1) to (11), wherein if a single coefficient is registered, the enhancement processing unit controls the enhancement process in accordance with the coefficient, and controls a degree of the enhancement process on the basis of the feature.

(15)

The image processing apparatus according to any one of (12) to (14), wherein the coefficient is generated in advance through machine learning.

(16)

The image processing apparatus according to any one of (1) to (15), wherein the image processing apparatus includes a control unit configured to cause a display unit to display the first image data subjected to the enhancement process.

(17)

The image processing apparatus according to (16), wherein the control unit causes the display unit to display both of the first image data before being subjected to the enhancement process and the first image data after being subjected to the enhancement process.

(18)

The image processing apparatus according to any one of (1) to (17), wherein the enhancement processing unit controls the degree of the enhancement process on the basis of operation information input from a user.

(19)

An image processing method comprising:
detecting a feature of first image data that is obtained by capturing an image of a blood vessel by ICG fluorescence imaging; and
controlling, by a processor, a degree of an enhancement process performed on the first image data, on the basis of the feature.

(20)

An image processing system comprising:
an imaging unit configured to capture an image of a blood vessel by ICG fluorescence imaging and obtain first image data;
a feature detecting unit configured to detect a feature of the first image data; and
an enhancement processing unit configured to control a degree of the enhancement process performed on the first image data on the basis of the feature.

REFERENCE SIGNS LIST

110 Object feature detecting unit
111 Degree-of-scattering detecting unit

112 Vascular diameter detecting unit
113 Vascular density detecting unit
114 Vascular depth detecting unit
115 Object feature vectorization processing unit
1111 Correlation value calculating unit
1112 Degree-of-scattering assigning unit
1121 First image processing unit
1122 Second image processing unit
1123 Difference calculating unit
1124 Vascular diameter assigning unit
1141 Blood vessel detecting unit
1142 Correlation value calculating unit
1143 Vascular depth assigning unit
120 Class classification unit
130 Coefficient selecting unit
140 Coefficient DB
160 Enhancement processing unit

The invention claimed is:

1. An image processing apparatus, comprising:
a processor configured to:
obtain first image data of a first image of a blood vessel, wherein the first image is captured by IndoCyanine Green (ICG) fluorescence imaging;
obtain second image data of a second image of the blood vessel, wherein the second image is captured by an application of white light;
calculate, based on a first difference value between the first image and the second image, a correlation value between the first image and the second image;
determine, based on the first image data and the second image data, a first feature that includes the calculated correlation value;
execute a first image process on the first image data at a first intensity;
execute a second image process on the first image data at a second intensity different from the first intensity;
determine a second feature that includes one of a vascular diameter or a second difference value between a result of the first image process and a result of the second image process, wherein the vascular diameter is based on the second difference value; and
control, based on at least one of the first feature or the second feature, a degree of an enhancement process on the first image data.

2. The image processing apparatus according to claim 1, wherein the processor is further configured to determine a degree of scattering based on the correlation value.

3. The image processing apparatus according to claim 2, wherein the processor is further configured to increase the degree of the enhancement process with one of a decrease in the correlation value or an increase in the degree of scattering.

4. The image processing apparatus according to claim 1, wherein the processor is further configured to increase the degree of the enhancement process with a decrease in one of an absolute value of the second difference value or the vascular diameter.

5. The image processing apparatus according to claim 1, wherein the processor is further configured to:
calculate an eigenvalue of a Hessian matrix from the first image data; and
determine the second feature that includes the vascular diameter, based on the eigenvalue of the Hessian matrix calculated from the first image data.

6. The image processing apparatus according to claim 5, wherein the processor is further configured to increase the degree of the enhancement process with a decrease in the vascular diameter.

7. The image processing apparatus according to claim 1, wherein the processor is further configured to determine a third feature that includes a vascular density, based on the first image data.

8. The image processing apparatus according to claim 7, wherein the processor is further configured to increase the degree of the enhancement process with an increase in the vascular density.

9. The image processing apparatus according to claim 1, wherein the processor is further configured to determine a third feature that includes a vascular depth, based on the correlation value and information indicating one of a presence or an absence of the blood vessel in at least one of the first image data or the second image data.

10. The image processing apparatus according to claim 9, wherein the processor is further configured to increase the degree of the enhancement process with an increase in the vascular depth.

11. The image processing apparatus according to claim 1, wherein in a case where a registration of a coefficient corresponding to the first feature is present, the processor is further configured to control the enhancement process based on the coefficient.

12. The image processing apparatus according to claim 1, wherein in a case where a registration of a coefficient corresponding to the first feature is present and a registration of a coefficient corresponding to the second feature that is different from the first feature is absent, the processor is further configured to:
control the enhancement process based on the coefficient corresponding to the first feature; and
control the degree of the enhancement process based on the second feature.

13. The image processing apparatus according to claim 1, wherein in a case where a registration of a single coefficient is present, the processor is further configured to:
control the enhancement process based on the single coefficient; and
control the degree of the enhancement process based on the first feature.

14. The image processing apparatus according to claim 11, wherein the processor is further configured to generate the coefficient corresponding to the first feature through machine learning.

15. The image processing apparatus according to claim 1, wherein the processor is further configured to cause a display unit to display the first image data subjected to the enhancement process.

16. The image processing apparatus according to claim 15, wherein the processor is further configured to cause the display unit to display both of the first image data before being subjected to the enhancement process and the first image data after being subjected to the enhancement process.

17. The image processing apparatus according to claim 1, wherein the processor is further configured to:
receive user operation information; and
control the degree of the enhancement process based on the user operation information.

18. An image processing method, comprising:
obtaining first image data of a first image of a blood vessel, wherein the first image is captured by IndoCyanine Green (ICG) fluorescence imaging;

obtaining second image data of a second image of the blood vessel, wherein the second image is captured by an application of white light;

calculating, based on a first difference value between the first image and the second image, a correlation value between the first image and the second image;

determining, based on the first image data and the second image data, a first feature that includes the calculated correlation value;

executing a first image processing on the first image data at a first intensity;

executing a second image processing on the first image data at a second intensity different from the first intensity;

determining a second feature that includes one of a vascular diameter or a second difference value between a result of the first image processing and a result of the second image processing, wherein the vascular diameter is based on the second difference value; and controlling, by a processor, a degree of an enhancement process on the first image data, based on the at least one of first feature or the second feature.

19. An image processing system, comprising:
an image sensor configured to:
- capture a first image of a blood vessel by IndoCyanine Green (ICG) fluorescence imaging; and
- capture a second image of the blood vessel by an application of white light; and a processor configured to:
- obtain first image data of the first image of the blood vessel;
- obtain second image data of the second image of the blood vessel;
- calculate, based on a first difference value between the first image and the second image, a correlation value between the first image and the second image;
- determine, based on the first image data and the second image data, a first feature that includes the calculated correlation value;
- execute a first image process on the first image data at a first intensity;
- execute a second image process on the first image data at a second intensity different from the first intensity;
- determine a second feature that includes one of a vascular diameter or a second difference value between a result of the first image process and a result of the second image process, wherein the vascular diameter is based on the second difference value; and
- control, based on at least one of the first feature or the second feature, a degree of an enhancement process on the first image data.

* * * * *